(12) United States Patent
Li et al.

(10) Patent No.: US 7,212,293 B1
(45) Date of Patent: May 1, 2007

(54) OPTICAL DETERMINATION OF PATTERN FEATURE PARAMETERS USING A SCALAR MODEL HAVING EFFECTIVE OPTICAL PROPERTIES

(75) Inventors: Guoguang Li, Fremont, CA (US); Shuqiang Chen, Sunnyvale, CA (US); Phillip Walsh, San Jose, CA (US)

(73) Assignee: n&k Technology, Inc., Santa Clara, CA (US)

( * ) Notice: Subject to any disclaimer, the term of this patent is extended or adjusted under 35 U.S.C. 154(b) by 387 days.

(21) Appl. No.: 10/859,252

(22) Filed: Jun. 1, 2004

(51) Int. Cl.
*G01B 11/24* (2006.01)

(52) U.S. Cl. .................... 356/610; 356/625

(58) Field of Classification Search ........ 356/601–625, 356/630, 634–636, 237.5; 250/559.22, 559.27, 250/225; 702/155, 166, 170
See application file for complete search history.

(56) References Cited

U.S. PATENT DOCUMENTS

| | | | |
|---|---|---|---|
| 4,112,309 A * | 9/1978 | Nakazawa et al. ..... 250/559.24 |
| 5,607,800 A * | 3/1997 | Ziger ........................... 430/8 |
| 5,861,320 A * | 1/1999 | Shiraishi ..................... 438/16 |
| 5,867,276 A | 2/1999 | McNeil et al. ............... 356/445 |
| 5,900,633 A | 5/1999 | Solomon et al. ........ 250/339.08 |
| 5,963,329 A | 10/1999 | Conrad et al. ............... 356/372 |
| 6,100,985 A | 8/2000 | Scheiner et al. ............ 356/381 |
| 6,281,974 B1 | 8/2001 | Scheiner et al. ............ 356/381 |
| 6,327,035 B1 | 12/2001 | Li et al. ...................... 356/432 |
| 6,340,602 B1 | 1/2002 | Johnson et al. ................ 438/7 |
| 6,433,878 B1 * | 8/2002 | Niu et al. .................... 356/603 |
| 6,476,920 B1 | 11/2002 | Scheiner et al. ............ 356/630 |
| 6,483,580 B1 | 11/2002 | Xu et al. ..................... 356/300 |
| 6,556,947 B1 | 4/2003 | Scheiner et al. ............ 702/172 |
| 6,590,656 B2 | 7/2003 | Xu et al. ..................... 356/369 |
| 6,609,086 B1 * | 8/2003 | Bao et al. .................... 702/189 |
| 6,623,991 B2 | 9/2003 | Johnson et al. ................ 438/7 |
| 6,657,736 B1 * | 12/2003 | Finarov et al. ............. 356/625 |
| 6,704,661 B1 | 3/2004 | Opsal et al. .................. 702/27 |
| 6,891,628 B2 * | 5/2005 | Li et al. ...................... 356/625 |
| 6,900,892 B2 * | 5/2005 | Shchegrov et al. ......... 356/369 |
| 7,084,900 B1 * | 8/2006 | Watanabe et al. ............. 348/94 |
| 2003/0058443 A1 | 3/2003 | Xu et al. ..................... 356/369 |

OTHER PUBLICATIONS

Sang-Jun Cho et al., "Etch depth control in bulk GaAs using patterning and real time spectroscopic ellipsometry," J. Vac. Sci. Technol. B 20(1), Jan./Feb. 2002, pp. 197-202.

(Continued)

*Primary Examiner*—Sang H. Nguyen
(74) *Attorney, Agent, or Firm*—Lumen Intellectual Property Services, Inc.

(57) ABSTRACT

Optical characterization of lateral features of a pattern is provided. A plane-wave optical response is calculated for each feature. At least one of these plane-wave responses is calculated from an effective optical property (e.g., a waveguide modal refractive index). Such effective optical properties depend on feature geometry and on intrinsic material optical properties. The plane-wave responses for each feature are combined to generate a modeled pattern response. By fitting the modeled pattern response to a corresponding measured pattern response, estimates for pattern feature parameters are obtained. The use of an effective optical property improves model accuracy, especially for features having a size on the order of a wavelength or less, without significantly increasing computation time.

28 Claims, 16 Drawing Sheets

OTHER PUBLICATIONS

M.E. Lee et al., "Analysis of Reflectometry and Ellipsometry Data from Patterned Structures," Dept. of Electrical Engineering and Computer Science, Univ. of Mich., pp. 1-5.

Helen L. Maynard et al., "Multiwavelength ellipsometry for real-time process control of the plasma etching of patterned samples," J. Vac. Sci. Technol. B 15(1), Jan./Feb. 1997 pp. 109-115.

Helen L. Maynard et al., "Thin-film interferometry of patterned surfaces," J. Vac. Sci. Technol. B 13(3), May/Jun. 1995, pp. 848-857.

M.G. Moharam et al., "Formulation of stable and efficient implementation of the rigorous coupled-wave analysis of binary gratings," J. Opt. Soc. Am. A/vol. 12, No. 5/May 1995 pp. 1068-1076.

M.G. Moharam et al., "Stable implementation of the rigorous coupled-wave analysis for surface-relief gratings: enhanced transmittance matrix approach," J. Opt. Soc. Am. A. vol. 12, No. 5/May 1995 pp. 1077-1086.

P.A. Heimann et al., "Optical Etch-Rate Monitoring: Computer Simulation of Reflectance," J. Electrochem. Soc.: Solid-State Science and Technology, vol. 131, No. 4 pp. 881-885.

P.A. Heimann, "Optical Etch-Rate Monitoring Using Active Device Areas: Lateral Interference Effects," J. Electrochem. Soc.: Solid-State Science and Technology, vol. 132, No. 8 pp. 2003-2006.

* cited by examiner

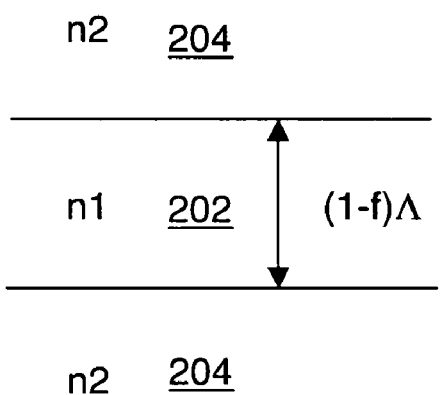
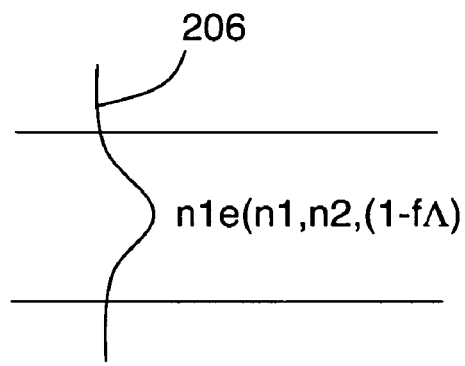
Fig. 2a                    Fig. 2b
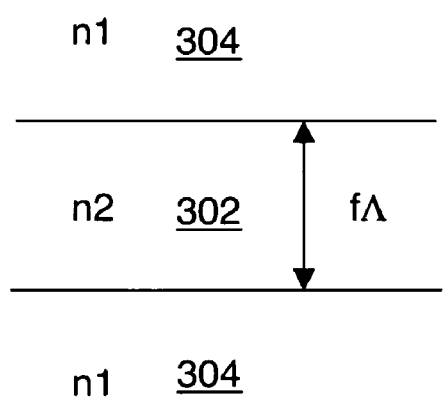
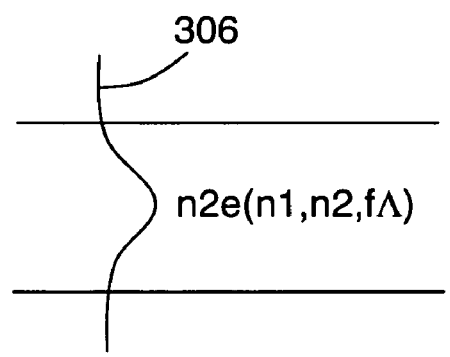
Fig. 3a                    Fig. 3b

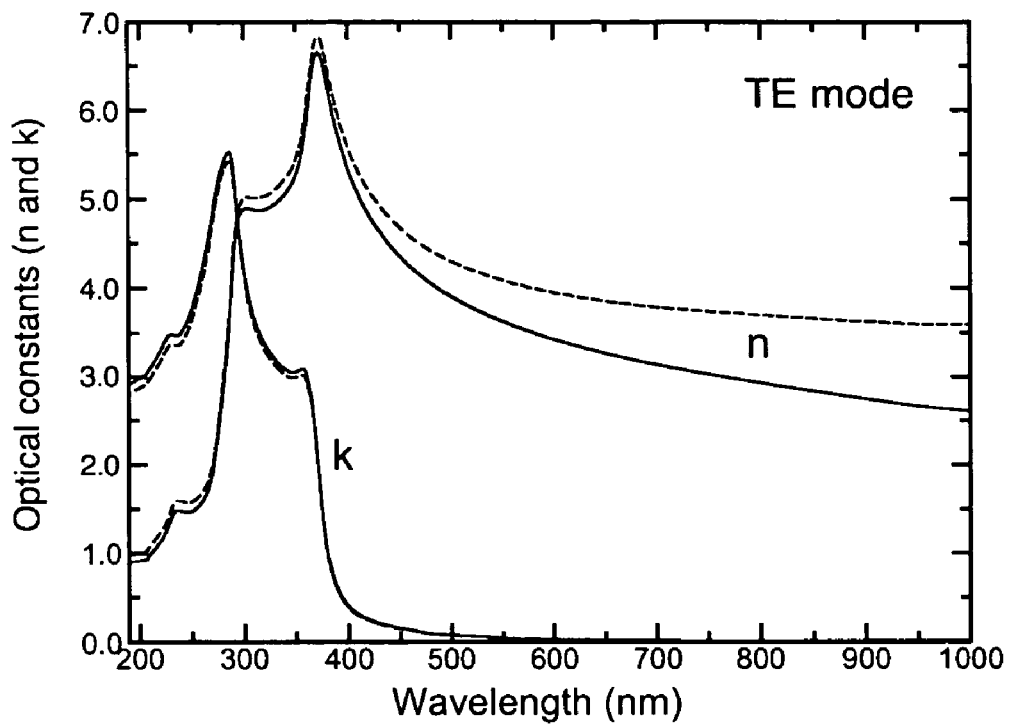
Fig. 4a (TE mode)
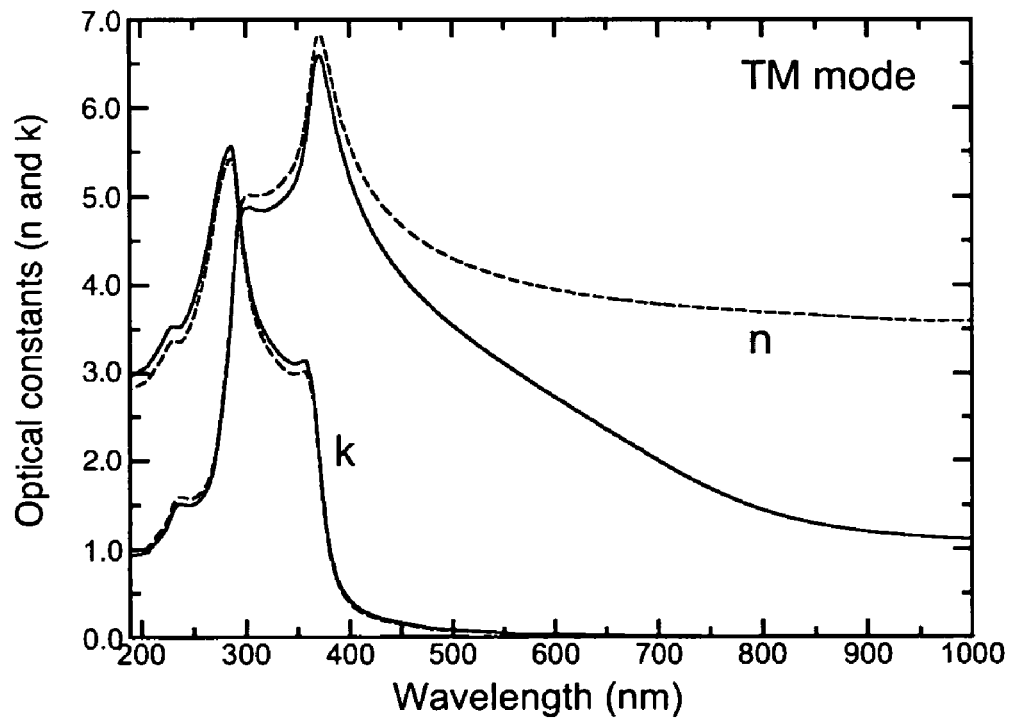
Fig. 4b (TM mode)

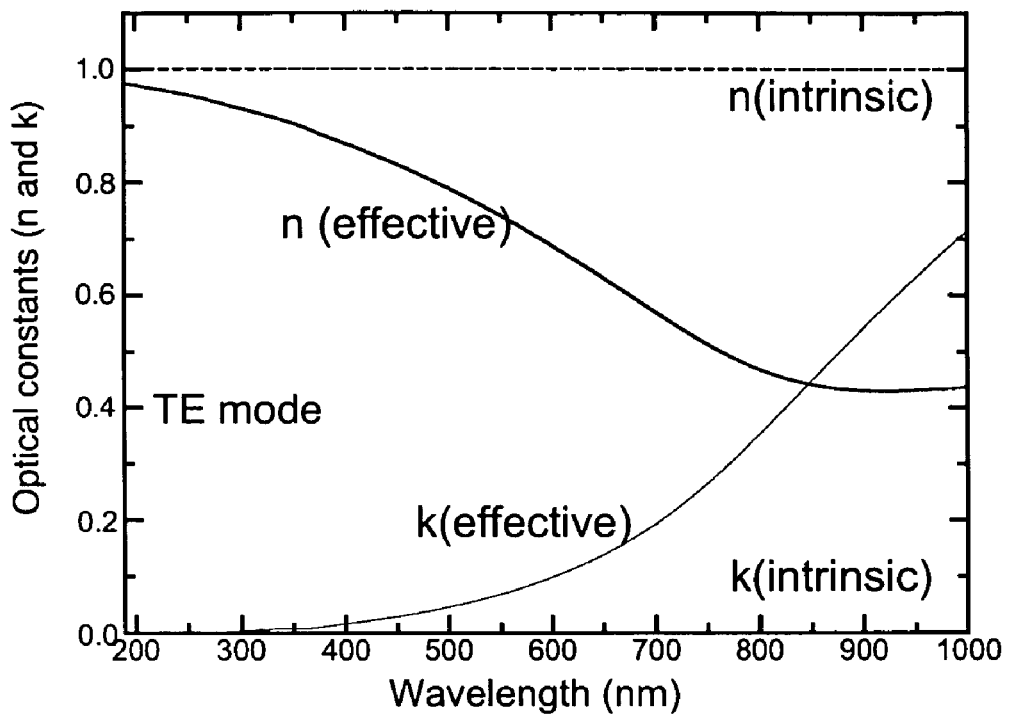
Fig. 5a (TE mode)
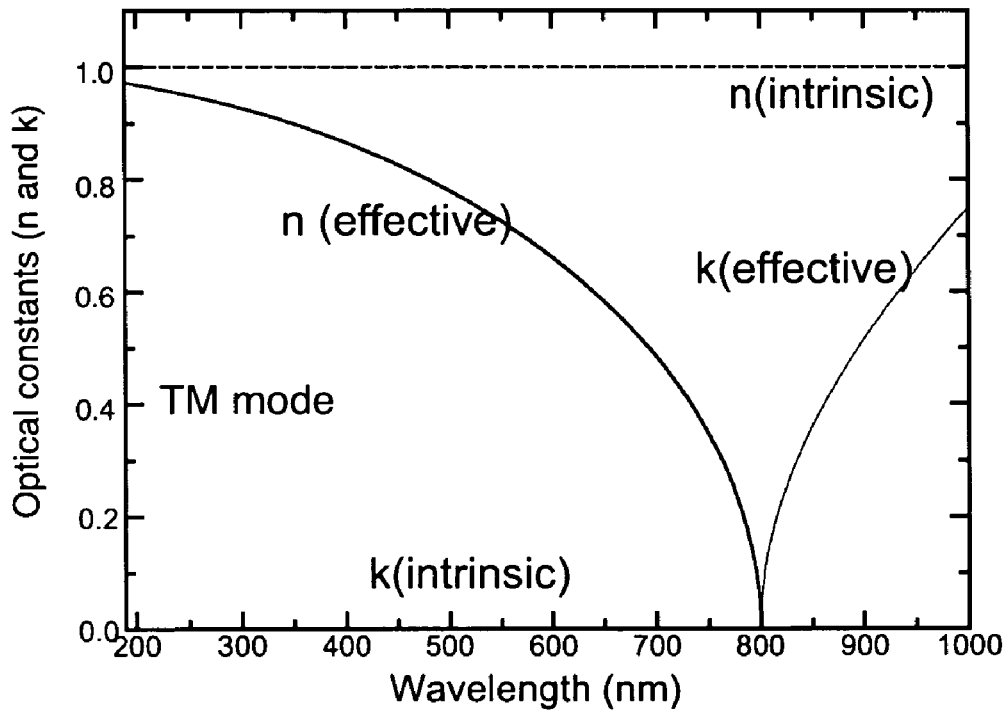
Fig. 5b (TM mode)

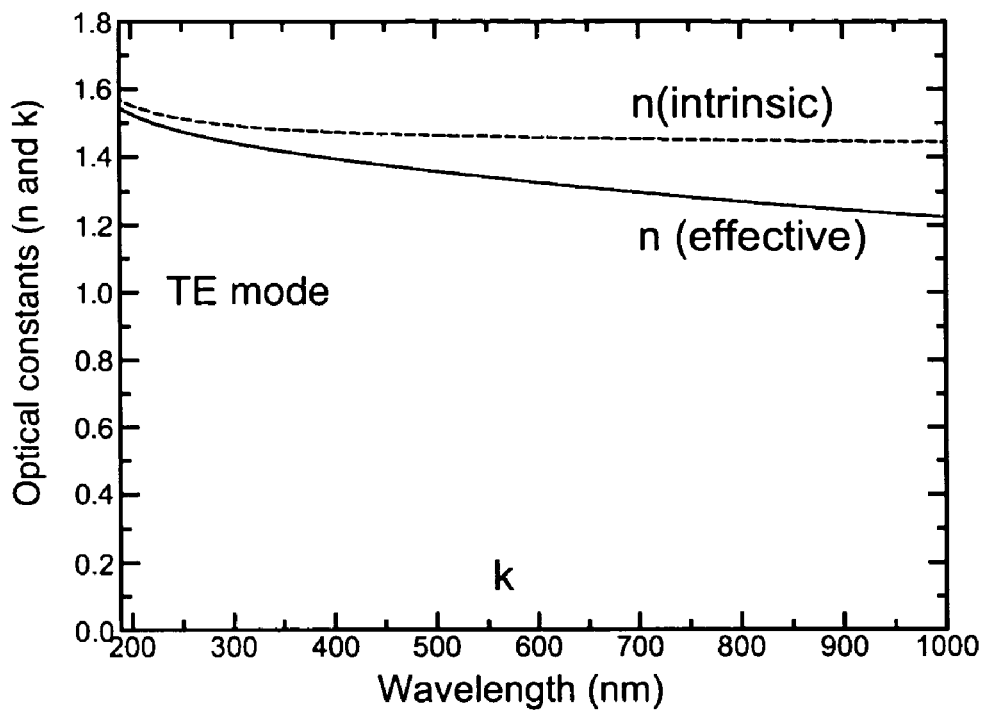
Fig. 6a (TE mode)
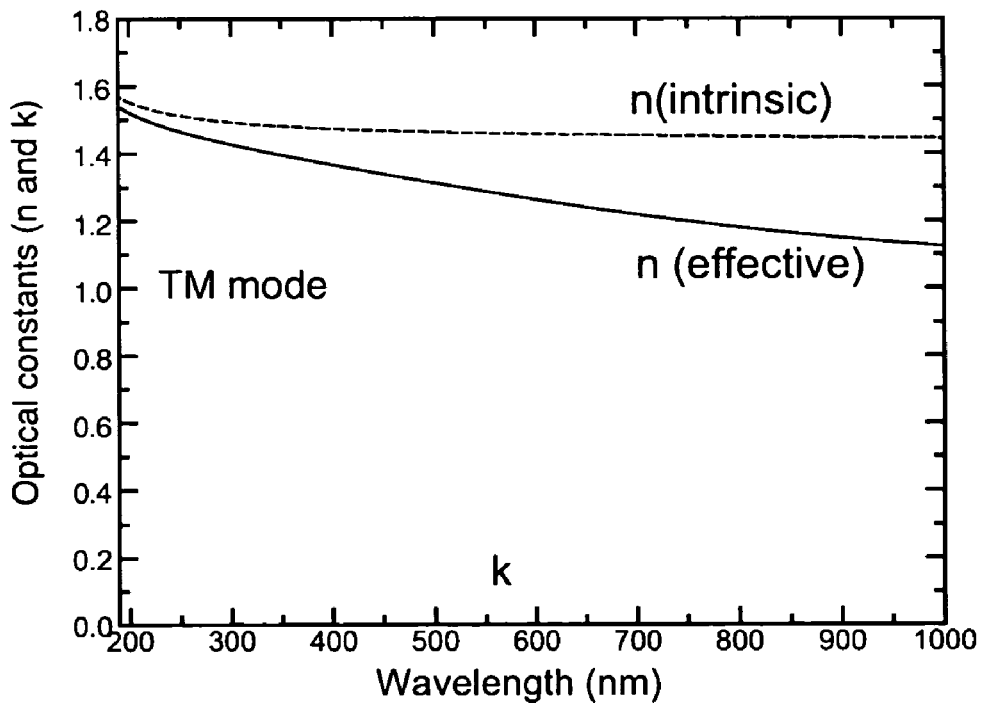
Fig. 6b (TM mode)

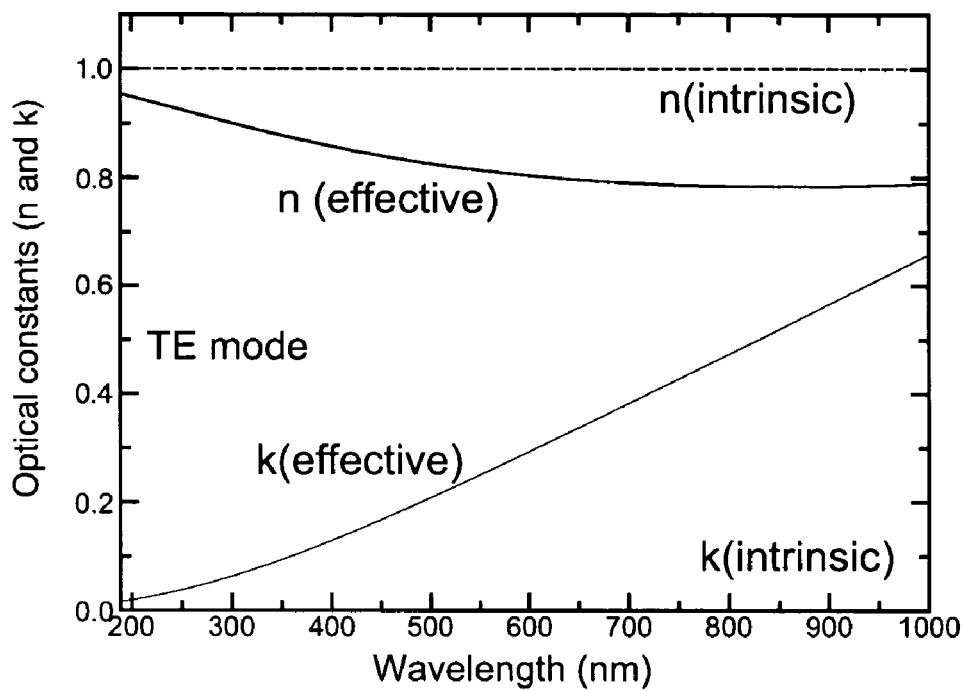
Fig. 7a (TE mode)
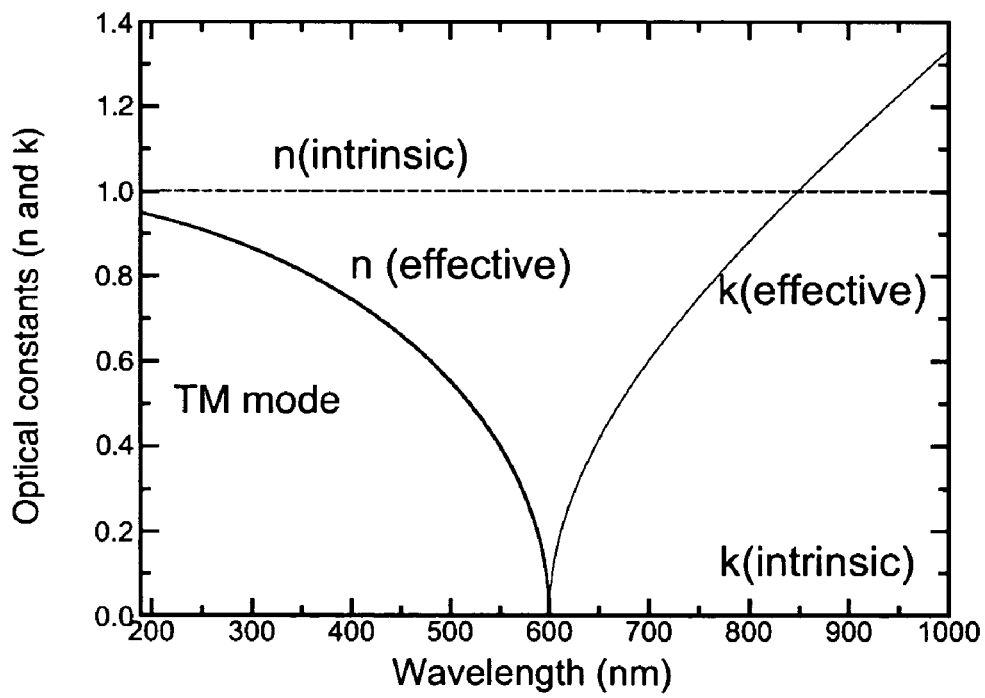
Fig. 7b (TM mode)

OPTICAL DETERMINATION OF PATTERN FEATURE PARAMETERS USING A SCALAR MODEL HAVING EFFECTIVE OPTICAL PROPERTIES

FIELD OF THE INVENTION

This invention relates to extraction of pattern feature parameters from optical measurements and modeling.

BACKGROUND

Manufacturing processes for producing products usually rely on quantitative measurements to provide information required for process control. Such measurements can be made on the final product, and/or on intermediate stages of the product within the manufacturing process, and/or on tools/fixtures used in the manufacturing process. For example, in semiconductor chip fabrication, measurements can be performed on finished chips (i.e., final product), on a wafer patterned with a photoresist (i.e., intermediate stage), or on a mask (i.e., a tool or fixture). Frequently, as in the case of semiconductor chip fabrication, these measurements are performed on structures having small dimensions. Furthermore, it is highly desirable to perform process control measurements quickly and non-destructively, in order to ensure a minimal impact on the process being controlled. Since optical measurements can be performed quickly, tend to be non-destructive, and can be sensitive to small features, various optical process control measurements have been developed.

Optical process control measurements can often be regarded as methods for measuring parameters of a pattern. For example, a pattern can be a periodic one-dimensional grating of lines on the surface of a wafer, and the parameters to measure can be line width, line spacing and depth of the grating. To measure these parameters, an optical response of the pattern is measured. For example, reflectance as a function of wavelength can be measured. Typically, the optical response will depend on the parameter (or parameters) of interest in a complicated way such that direct parameter extraction from measured data is impractical. Instead, a mathematical model is typically constructed for the pattern, having the parameters of interest as variables. Within the model, a modeled optical response is calculated corresponding to the measured optical response. The parameters of interest are then determined by adjusting the variables to fit the modeled response to the measured response. Various optical process control measurements differ depending on the measured response(s), and on the kind of mathematical model employed.

In particular, the mathematical model employed for such measurements can be more or less rigorous. Generally, more rigorous models provide improved fidelity between measured and modeled results, but require greater calculation time and/or processing resources. In addition, rigorous models can require more detailed measurements, which tends to increase measurement time and/or cost. Less rigorous models reduce calculation time and/or required processing resources, but tend to provide reduced fidelity between measured and modeled results.

A rigorous modeling approach described by Moharam et al. in Journal of the Optical Society of America (JOSA), A12, n5, p 1068–1076, 1995 is known as the rigorous coupled wave analysis (RCWA). The RCWA is limited to periodic structures such as a grating, and the required computation time is generally large, especially for a grating having a period substantially larger than a wavelength. Rigorous modeling approaches other than the RCWA have also been developed, but such approaches have similar advantages and drawbacks as the RCWA. The RCWA was first introduced by K. Knop in JOSA, v68, p 1206, 1978, and was later greatly improved by Moharam et al. in the above-referenced article. Some implementations of the RCWA are described in U.S. Pat. Nos. 6,590,656 and 6,483,580 assigned to KLA-Tencor, U.S. Pat. No. 5,963,329 assigned to IBM, and U.S. Pat. No. 5,867,276 assigned to Bio-Rad.

An example of a less-rigorous modeling approach is referred to herein as the scalar model. The basic idea of the scalar model is to divide the pattern of interest into several features, calculate an optical response (e.g., complex amplitude reflection or transmission coefficient) of each feature in a plane-wave approximation (i.e., as if each feature had infinite lateral extent), and then combine the calculated plane-wave responses of each feature to obtain an approximate modeled response for the pattern. For example, if features 1 and 2 have plane-wave complex amplitude reflection coefficients r1 and r2 respectively, where r1 and r2 are referred to the same reference plane, then the combined reflectance R in the scalar model is given by $R=|a1r1+a2r2|^2$, assuming lateral coherence. Here a1 and a2 are the areal fractions of features 1 and 2 respectively (i.e., the fraction of the total pattern area in features 1 and 2 respectively). Thus diffraction is ignored in the scalar model, but interference between features can be accounted for.

The scalar model was originally proposed by Heimann et al. (Journal of the Electrochemical Society, v131, p 881, 1984; ibid, v132, p 2003, 1985). Applications of the scalar model are considered by Cho et al. (Journal of Vacuum Science and Technology (JVST), B20, p 197, 2002), Maynard et al. (JVST, B13, p 848, 1995; JVST, B15, p 109, 1997), and Lee et al. (International Conference on Characterization and Metrology for ULSI Technology, Gaithersburg, Md., Mar. 23–27 1998, AIP conf. proc., v449, p 331, 1998). Aspects of the scalar model are considered in U.S. Pat. Nos. 6,281,974 and 6,100,985 by Scheiner et al., assigned to Nova Measuring Instruments Ltd.; U.S. Pat. Nos. 6,623,991 and 6,340,602 by Johnson et al. assigned to Therma-Wave Inc. and Sensys Instruments respectively; and U.S. patent application Ser. No. 10/607,410 by Li et al. entitled "Method and Apparatus for Examining Features on Semi-Transparent Substrates" and assigned to n&k Technology Inc.

This conventional scalar model works well for large features (i.e., features substantially larger than an optical wavelength), but its accuracy decreases with feature size, and it typically does not provide sufficiently accurate results for features having a size on the order of a wavelength or smaller. However, the scalar model is much simpler than rigorous modeling approaches, such as the RCWA, and thus requires far less computation time and/or processor resources. Accordingly, it would be an advance in the art to improve the accuracy of the scalar model for features having small size.

Thus an object of the present invention is to provide a model having improved accuracy compared to the scalar model for patterns having small feature sizes. A further object of the invention is to provide a model having reduced computation time compared to rigorous modeling approaches, such as the RCWA. Yet another object of the invention is to achieve the preceding two objects simultaneously.

SUMMARY

The present invention provides optical characterization of lateral features of a pattern. A plane-wave optical response is calculated for each feature. At least one of these plane-wave responses is calculated from an effective optical property (e.g., a waveguide modal refractive index). Such effective optical properties depend on feature geometry and on intrinsic material optical properties. The plane-wave responses for each feature are combined to generate a modeled pattern response. By fitting the modeled pattern response to a corresponding measured pattern response, estimates for pattern feature parameters are obtained. The use of an effective optical property improves model accuracy, especially for features having a size on the order of a wavelength or less, without significantly increasing computation time.

BRIEF DESCRIPTION OF THE DRAWINGS

FIGS. 2a and 2b show a planar waveguide model of the trenches of FIG. 1a according to an embodiment of the invention.

FIGS. 3a and 3b show a planar waveguide model of the lines of FIG. 1a according to an embodiment of the invention.

FIGS. 4a and 4b show calculated TE and TM planar waveguide modal refractive indices respectively (solid lines). Dashed lines show the core intrinsic refractive index. The core is 0.1 μm Si, and the cladding is air.

FIGS. 5a and 5b show calculated TE and TM planar waveguide modal refractive indices respectively (solid lines). Dashed lines show the core intrinsic refractive index. The core is 0.3 μm air, and the cladding is Si.

FIGS. 6a and 6b show calculated TE and TM planar waveguide modal refractive indices respectively (solid lines). Dashed lines show the core intrinsic refractive index. The core is 0.3 μm $SiO_2$, and the cladding is air.

FIGS. 7a and 7b show calculated TE and TM planar waveguide modal refractive indices respectively (solid lines). Dashed lines show the core intrinsic refractive index. The core is 0.3 μm air, and the cladding is $SiO_2$.

DETAILED DESCRIPTION

Figure 1A:
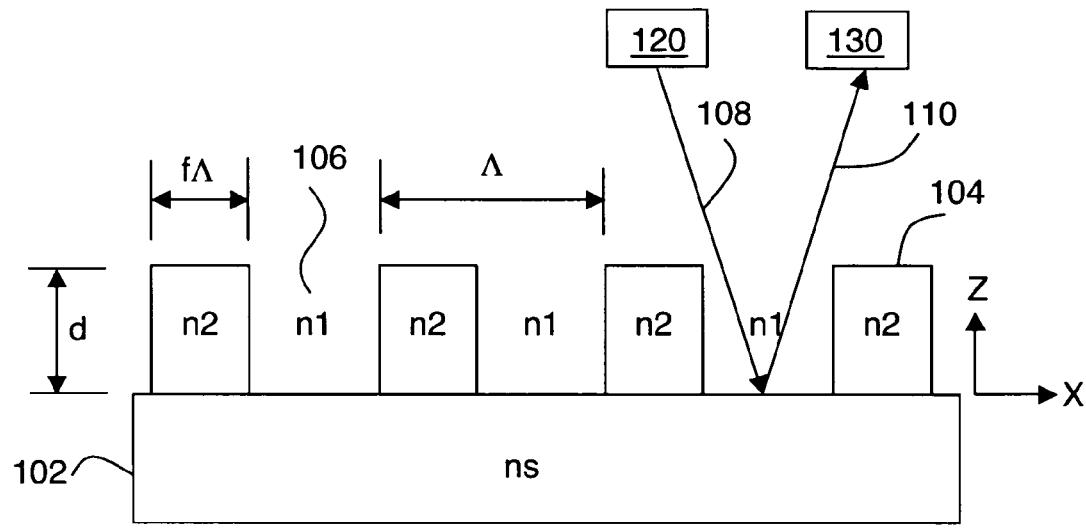
FIG. 1a shows a side view of a one-dimensional grating structure.

FIG. 1a shows a side view of a one-dimensional grating structure. The structure of FIG. 1 is a representative example of a patterned structure having features amenable to optical characterization. The example of FIG. 1 shows a periodic, one-dimensional grating structure having alternating lines 104 and trenches 106 with refractive indices n2 and n1 respectively. The grating period is Λ, and lines 104 have a width of fΛ, where 0<f<1. Lines 104 and trenches 106 are disposed on top of a substrate 102 having a substrate refractive index ns, and have a thickness (or depth) d. Optical measurements are performed on the structure of FIG. 1 by illuminating it with an incident light beam 108, and measuring a reflected light beam 110. Incident light beam 108 is provided by a source 120, and reflected light beam 110 is received by a detector 130. Preferably, such measurements are performed over a range of incident wavelengths (i.e., spectral measurements are performed) in order to provide sufficient measured data for feature parameter estimation. Typically, several features are illuminated simultaneously, since characterization of micro-scale features is of particular interest.

The conventional scalar model can be applied to the structure of FIG. 1a as follows. A plane wave response is calculated for the lines and the trenches individually, as if each feature had infinite lateral extent. For example, the line response r2 can be the plane wave amplitude reflection coefficient of a planar layer of thickness d and refractive index n2 disposed on top of a semi-infinite substrate having a refractive index of ns. The trench response r1 can be the plane wave amplitude reflection coefficient of a planar layer of thickness d and refractive index n1 disposed on top of a semi-infinite substrate having a refractive index of ns. In the calculation of responses r1 and r2, the angle of incidence and polarization are the same as for incident light beam 108 (i.e., the calculations correspond to the measurement conditions).

Once the line and trench responses r2 and r1 are calculated, they are combined to obtain a modeled response, which in this example is reflectance. There are various ways to combine the line and trench responses. For example, coherent combining is appropriate when the incident light beam 108 is laterally coherent, and in this case, the modeled reflectance $R_c = |f\, r2 + (1-f)\, r1|^2$. Alternatively, incoherent combining is appropriate when incident light beam 108 is not laterally coherent (i.e., it has a coherence length much less than lateral feature dimensions), and in this case, the modeled reflectance $R_i = f|r2|^2 + (1-f)|r1|^2$. In cases where the incident light is partially coherent, a simple reflectance model is $R = f_c R_c + (1-f_c) R_i$, where $R_c$ and $R_i$ are given above, and $f_c$ is a coherent fraction of the incident light. Note that in this example, responses are combined according to areal fraction (i.e., the line areal fraction is f, and the trench areal fraction is 1−f, and these factors are used in the above equations for combined reflectance). Further details on combining responses for coherent, incoherent and partially coherent incident light are given in U.S. patent application Ser. No. 10/607,410 by Li et al. entitled "Method and Apparatus for Examining Features on Semi-Transparent Substrates", hereby incorporated by reference in its entirety.

Since the modeled reflectance depends on parameters such as n1, n2, d, and f, one or more of these parameters can be estimated by fitting the modeled reflectance to the measured reflectance. Frequently, it is reasonable to regard the refractive indices n1 and n2 as known quantities, and extract estimates for d and f by fitting. For example, the trench index n1 is typically unity, and n2 is often well known (e.g., if the lines are Si or $SiO_2$). Note that the grating pitch $\Lambda$ is not a parameter in this conventional scalar model. Thus, to obtain feature sizes (e.g., $f\Lambda$ and/or $(1-f)\Lambda$) from a fitted areal fraction f, the grating pitch $\Lambda$ must also be known. In some cases (e.g., holographic photoresist exposure with known wavelength and exposure geometry), the grating pitch is known without need for a separate measurement. In other cases, a separate measurement can be performed to determine the grating pitch.

As indicated above, this conventional scalar model works well if the feature sizes (i.e., $f\Lambda$ and $(1-f)\Lambda$) are substantially larger than an optical wavelength (over the range of wavelengths measured). However, in practice it is frequently desirable to extract pattern feature parameters from patterns having features on the order of a wavelength in size (or even less). In these cases, the conventional scalar model typically does not provide sufficiently accurate results.

Figure 1B:
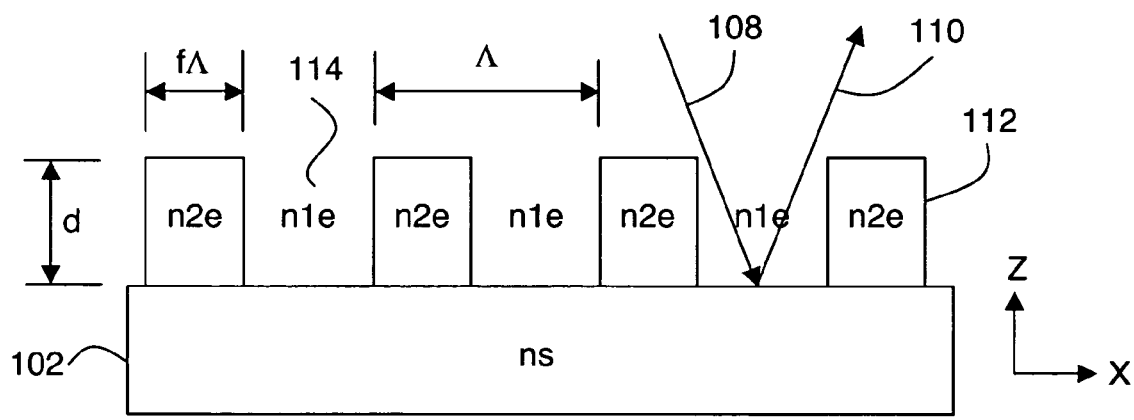
FIG. 1b shows a model of the structure of FIG. 1a according to an embodiment of the invention.

FIG. 1b shows a model of the structure of FIG. 1a according to an embodiment of the invention having a waveguide scalar model providing improved accuracy. FIG. 1b is the same as FIG. 1a, except that lines 104 on FIG. 1a having index n2 are modeled as lines 112 on FIG. 1b having effective index n2e. Similarly trenches 106 on FIG. 1a having index n1 are modeled as trenches 114 on FIG. 1b having effective index n1e. In this example, effective refractive indices n1e and n2e are waveguide modal indices for symmetric planar waveguides pertaining to trenches 106 and lines 104 respectively.

FIG. 2a shows a planar waveguide model pertaining to trenches 106 on FIG. 1a. On FIG. 2a a core 202 having index n1 (i.e., the trench index) is sandwiched between two semi-infinite cladding regions 204 having index n2 (i.e., the line index). The waveguide core width is $(1-f)\Lambda$. The waveguide of FIG. 2a supports a fundamental (or lowest order) mode 206 on FIG. 2b having a modal refractive index n1e. This modal refractive index is a function of material intrinsic optical properties (e.g., n1 and n2), and is also a function of feature geometry (e.g., $(1-f)\Lambda$). The modal refractive index is also a function of wavelength.

FIG. 3a shows a planar waveguide model pertaining to lines 104 on FIG. 1a. On FIG. 3a a core 302 having index n2 (i.e., the line index) is sandwiched between two semi-infinite cladding regions 304 having index n1 (i.e., the trench index). The waveguide core width is $f\Lambda$. The waveguide of FIG. 3a supports a fundamental (or lowest order) mode 306 on FIG. 3b having a modal refractive index n2e. This modal refractive index is a function of material intrinsic optical properties (e.g., n1 and n2), and is also a function of feature geometry (e.g., $f\Lambda$). The modal refractive index is also a function of wavelength.

Calculation of plane-wave responses r1 and r2 proceeds as discussed in connection with FIG. 1a, except for the substitution of effective indices n1e and n2e for n1 and n2 respectively. Combination of r1 and r2 according to the scalar model is also as indicated in connection with FIG. 1a. Thus, an embodiment of the invention can be practiced by substituting one or more effective optical properties (e.g., n1e and/or n2e) dependent on intrinsic material optical properties (e.g., n1 and n2) and on feature geometry (e.g., f, $\Lambda$) into an otherwise conventional scalar model. The resulting waveguide scalar model provides improved accuracy, as shown below, without significantly increasing computation time.

As indicated above, the conventional scalar model does not directly provide feature size information. Instead, areal fractions are determined, which can be used to determine feature sizes only if other information (e.g., pitch) is provided. In contrast, the waveguide scalar model directly provides feature size information, since waveguide core width is a fitting parameter of the waveguide scalar model. Feature sizes can be parameterized in various mathematically equivalent ways, such as line width and trench width, or trench width and trench areal fraction. Generally, any two independent geometric parameters will suffice to parameterize feature sizes of a periodic 1-D grating.

In cases where a grating has relatively wide lines, such that waveguide corrections to the lines are negligible, trench width and trench areal fraction are especially convenient fitting parameters. In such cases, trench width and trench areal fraction enter the waveguide scalar model independently. The trench width enters into the effective index, and the trench areal fraction enters when combining responses. If the lines are narrower than the trenches, the roles of lines and trenches in the preceding description can be reversed. Since waveguide corrections are increasingly significant as feature size decreases, it is preferred to parameterize the narrower of the two features of a 1-D grating, as indicated.

This improved waveguide scalar model can be more clearly appreciated in view of the following physical considerations. Illumination of a pattern such as shown on FIG. 1a will generally lead to the excitation of a large number of waveguide modes. In circumstances which most closely approximate the plane-wave idealization (i.e., normal or near-normal incidence of a well-collimated beam), the lowest order waveguide mode will typically be the dominant mode, and excitation of other waveguide modes will typically be negligible. Thus, the "best" refractive index to use in a plane-wave approximation should be the lowest order waveguide modal index, as in the above waveguide scalar model, instead of an intrinsic material index. Furthermore, interaction between neighboring lines (or neighboring trenches) is neglected in this waveguide scalar model. In context, this neglect of interactions is reasonable, since the scalar model itself relies on negligible interaction between features. A further consequence of neglect of interactions is that each waveguide can be, and preferably is, modeled as having an infinite homogeneous cladding.

Appendix A provides a detailed discussion of effective modal refractive index calculations for symmetric planar waveguides. Numerical examples are given on FIGS. 4a–7b. On these plots, n is the real part of the complex refractive index, and k is the imaginary part of the complex refractive index. Positive k indicates attenuation during propagation. Note that both intrinsic and effective refractive indices can be real or complex quantities, depending on whether or not loss is negligible. The calculations of FIGS. 4a–b and 5a–b relate to an exemplary grating structure having 0.1 µm Si lines separated by 1.9 µm air trenches. The calculations of FIGS. 6a–b and 7a–b relate to an exemplary grating structure having 0.3 µm $SiO_2$ lines separated by 1.7 µm air trenches. In these examples, an infinite cladding is assumed, as indicated above.

FIGS. 4a and 4b show calculated TE and TM planar waveguide modal refractive indices respectively (solid lines). Dashed lines show the core intrinsic refractive index.

The core is 0.1 µm Si, and the cladding is air. Note that the modal refractive index differs significantly from the core intrinsic refractive index, especially at longer wavelengths. Here the waveguide mode is a guided mode, since the core index is larger than the cladding index.

FIGS. 5a and 5b show calculated TE and TM planar waveguide modal refractive indices respectively (solid lines). Dashed lines show the core intrinsic refractive index. The core is 0.3 µm air, and the cladding is Si. Here the waveguide mode is a leaky mode, since the core index is less than the cladding index. Since the relevant waveguide mode is a leaky mode, the effective modal refractive index has large loss at long wavelengths. Physically, this loss accounts for radiation that leaks out of the air core and is lost to the cladding.

FIGS. 6a and 6b show calculated TE and TM planar waveguide modal refractive indices respectively (solid lines). Dashed lines show the core intrinsic refractive index. The core is 0.3 µm $SiO_2$, and the cladding is air. Note that the modal refractive index differs significantly from the core intrinsic refractive index, especially at longer wavelengths. Here the waveguide mode is a guided mode, since the core index is larger than the cladding index.

FIGS. 7a and 7b show calculated TE and TM planar waveguide modal refractive indices respectively (solid lines). Dashed lines show the core intrinsic refractive index. The core is 0.3 µm air, and the cladding is $SiO_2$. Here the waveguide mode is a leaky mode, since the core index is less than the cladding index. Since the relevant waveguide mode is a leaky mode, the effective modal refractive index has large loss at long wavelengths. Physically, this loss accounts for radiation that leaks out of the air core and is lost to the cladding.

FIGS. 8a–c, 9a–c, 10a–b and 11a–b show results of various exemplary calculations relating to conventional and waveguide scalar models. In all of these calculations, the RCWA method is used as a standard for comparison, since it is known to provide accurate results. Thus, performance of conventional and waveguide scalar models is evaluated in terms of how well their results match the RCWA results. Results are compared directly on FIGS. 8a–b and 9a–b, while the remaining figures relate to cases where a scalar model is use to estimate parameters by fitting scalar model results to RCWA results. The accuracy of the resulting estimates is a measure of scalar model performance. In all of these calculations, the modeled plane-wave reflectance is obtained by coherent combination of feature responses. Finally, the waveguide model is applied only to the trenches in these calculations, since the lines are sufficiently wide that waveguide corrections are negligible.

Figure 8A:
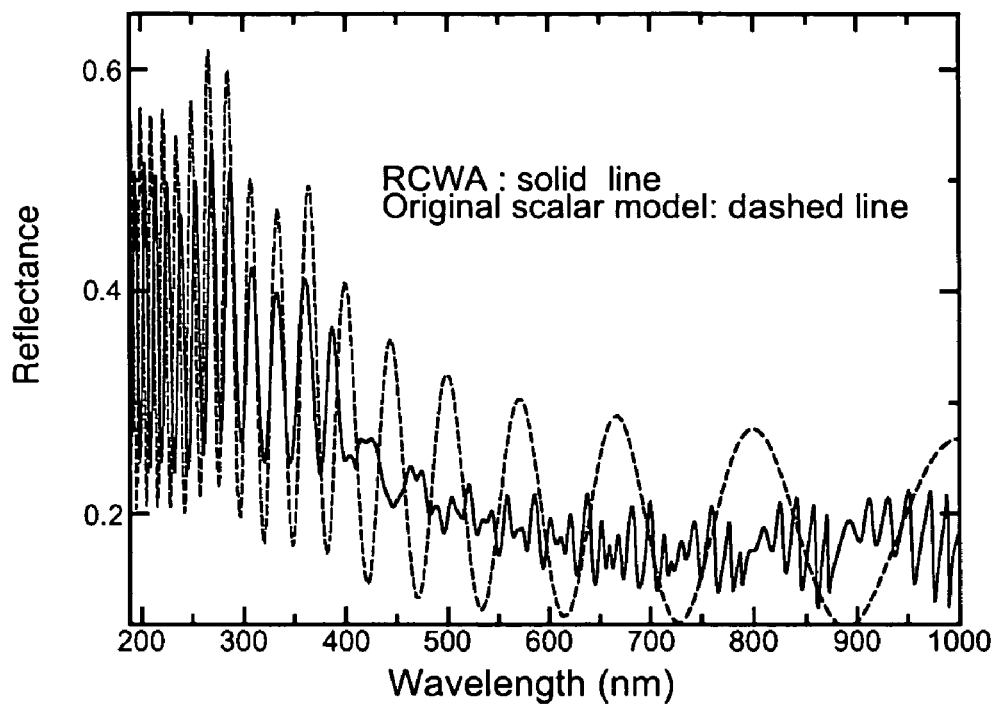
FIGS. 8a–c compare calculated RCWA results to results from a prior art scalar model approach for a first example.
Figure 8B:
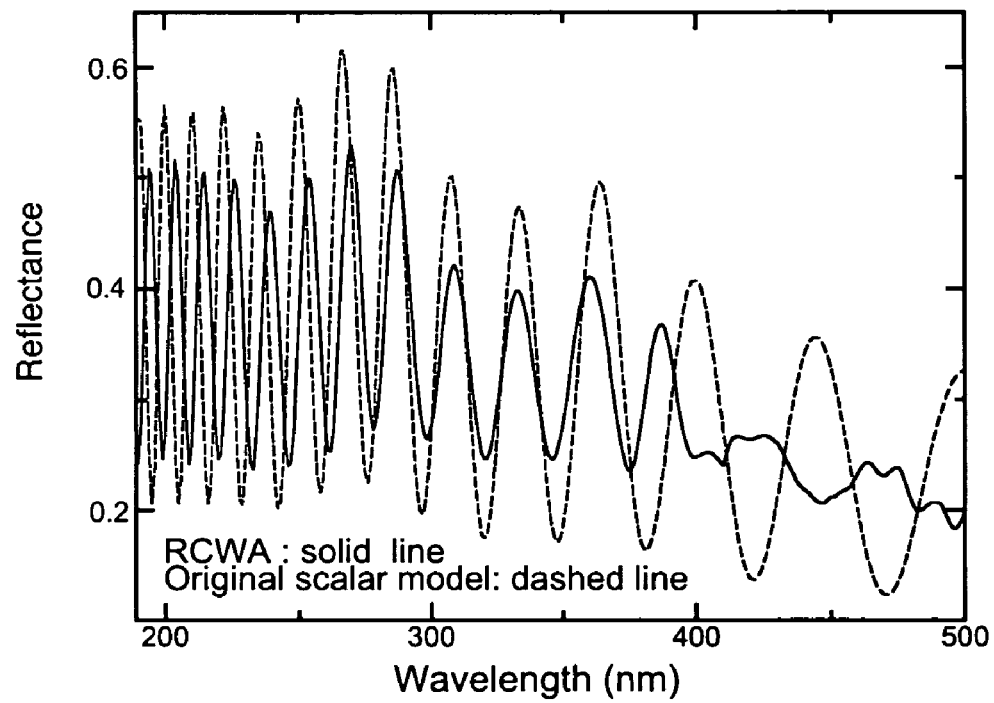
Figure 8C:
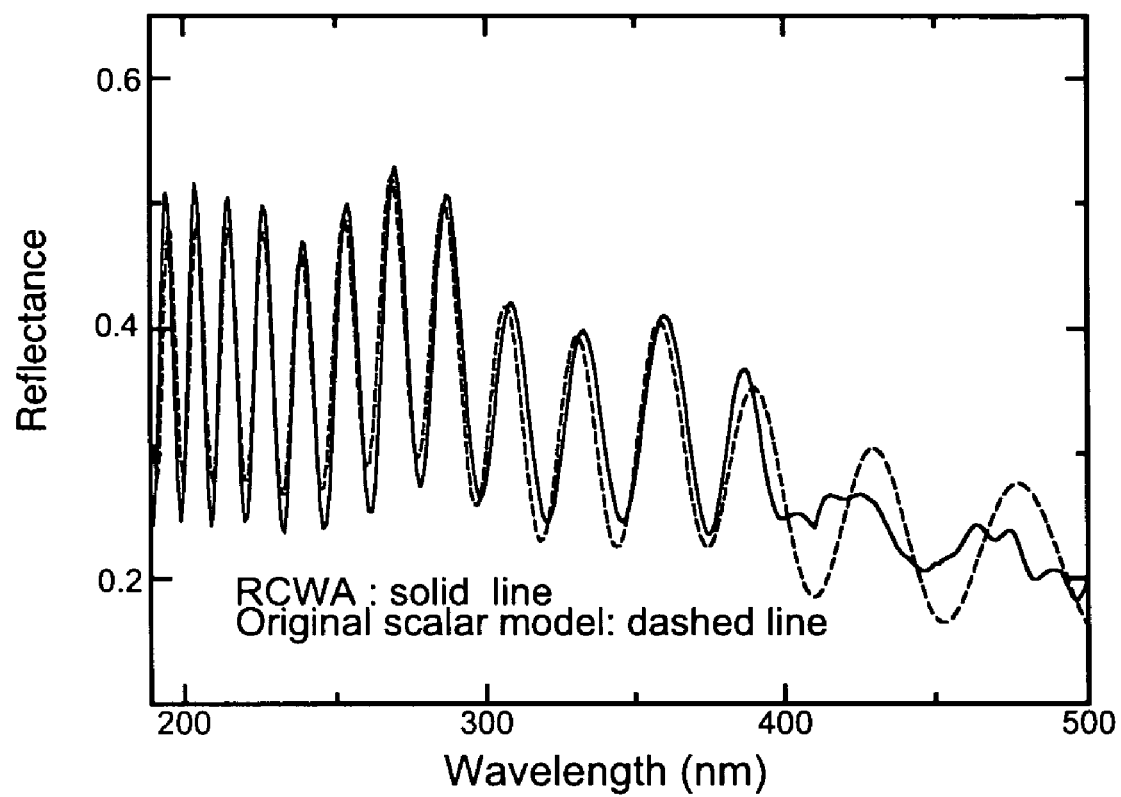

FIGS. 8a–c compare calculated RCWA results to results from a conventional scalar model approach for a first example. In this first example, light is normally incident and TE polarized on a 2 µm deep grating having 1.6 µm Si lines and 0.4 µm air trenches (thus Λ=2 µm). This grating is on a Si substrate. FIGS. 8a and 8b show a comparison between RCWA results (solid line) and conventional scalar model results (dashed line) using the above parameter values. The conventional scalar model results differ significantly from the RCWA results. For example, on FIG. 8b, the two curves are out of phase at short wavelengths. FIG. 8c shows a comparison between RCWA results using the above parameters, and conventional scalar model results where parameter values are adjusted to fit to the RCWA results. Although a reasonable fit for wavelengths less than 400 nm is seen on FIG. 8c, the estimated depth value is 2.1496 µm, which is significantly different than the true depth of 2.0 µm.

Figure 9A:
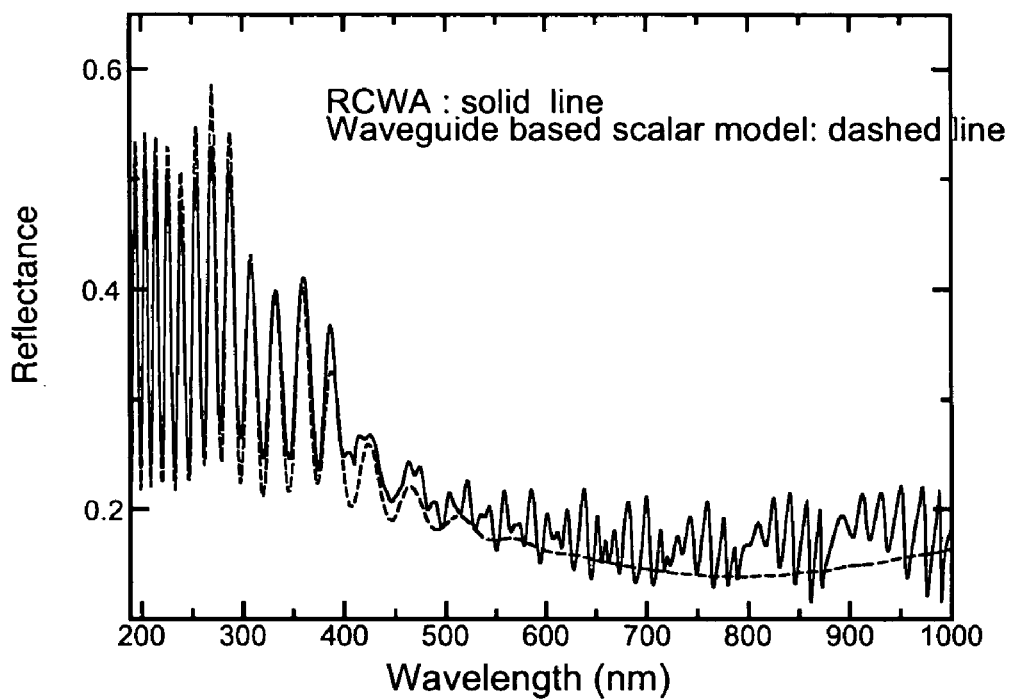
FIGS. 9a–c compare calculated RCWA results to results according to the present invention for the first example.
Figure 9B:
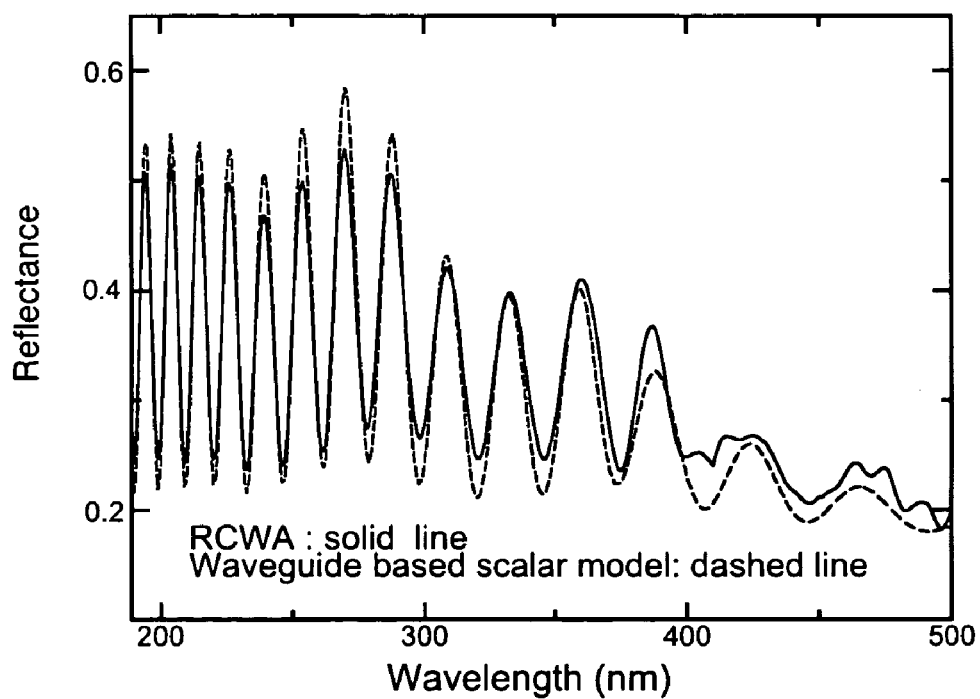
Figure 9C:
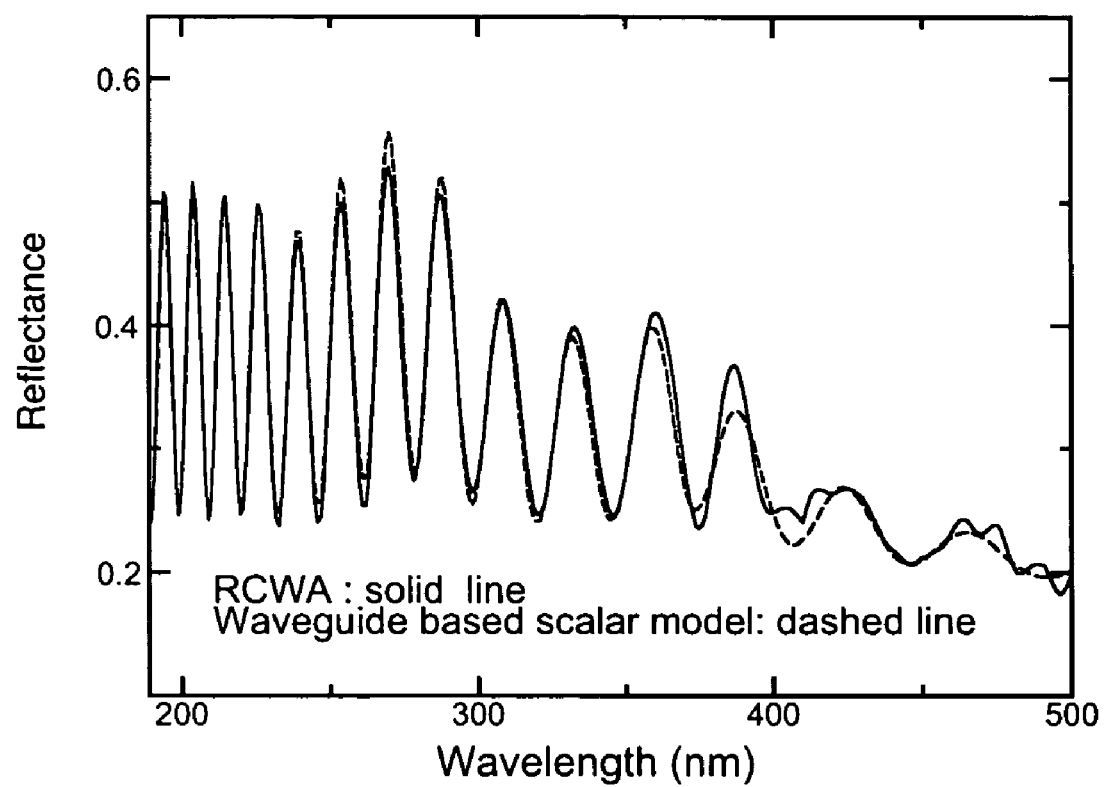

FIGS. 9a–c compare calculated RCWA results to results from a waveguide scalar model according to the invention for the above first example. FIGS. 9a and 9b show a comparison between RCWA results (solid line) and waveguide scalar model results (dashed line) using the above parameter values. The results of the waveguide scalar model are nearly featureless (i.e., oscillations are not present) for wavelengths longer than about 500 nm. This lack of features is due to the high effective k for the trench waveguide modal index at long wavelengths (e.g., as shown on FIGS. 5a and 7a). However, the waveguide scalar model results and RCWA results are in good agreement at wavelengths less than about 500 nm.

FIG. 9c shows a comparison between RCWA results using the above parameters, and waveguide scalar model results where parameter values are adjusted to fit to the RCWA results. A close fit to the RCWA results is seen on FIG. 9c, and the resulting estimated parameter values are as follows: grating depth=1.9983 µm, trench width=0.401 µm and trench areal fraction=0.164. The estimates for grating depth and line width provided by the waveguide scalar model are extremely accurate. Corrections to improve the accuracy of the estimated areal fraction will be considered below. The waveguide scalar model of the present invention does not require extensive calculations. For example, the waveguide scalar model results of FIG. 9a are obtained in less than 1 percent of the computation time required to obtain the RCWA results of FIG. 9a.

Figure 10A:
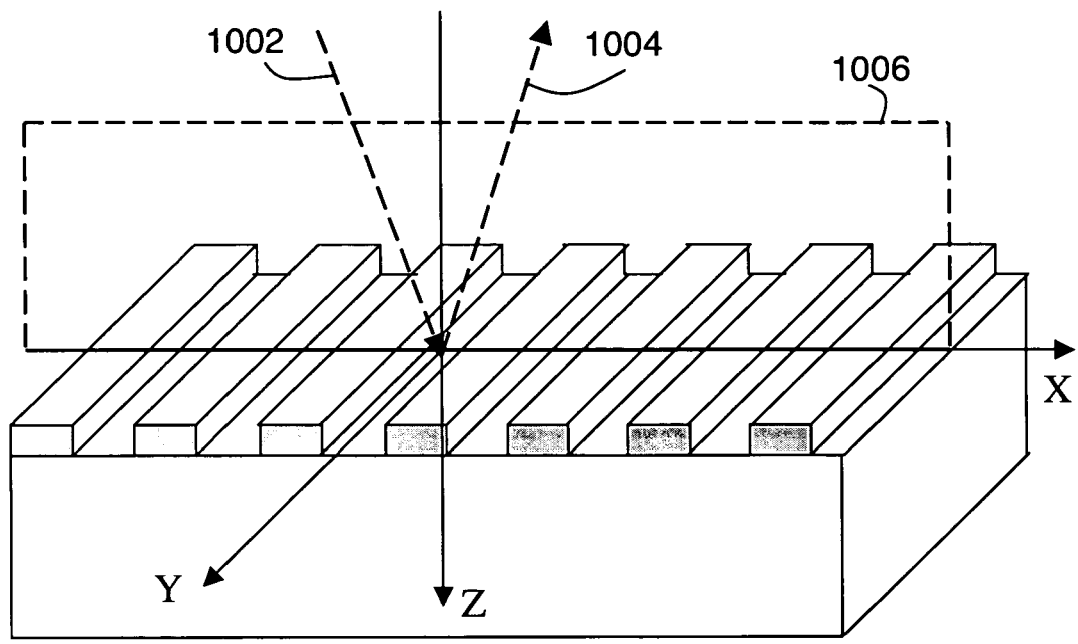
FIG. 10a shows illumination of a grating structure with a plane of incidence perpendicular to the grating lines.
Figure 10B:
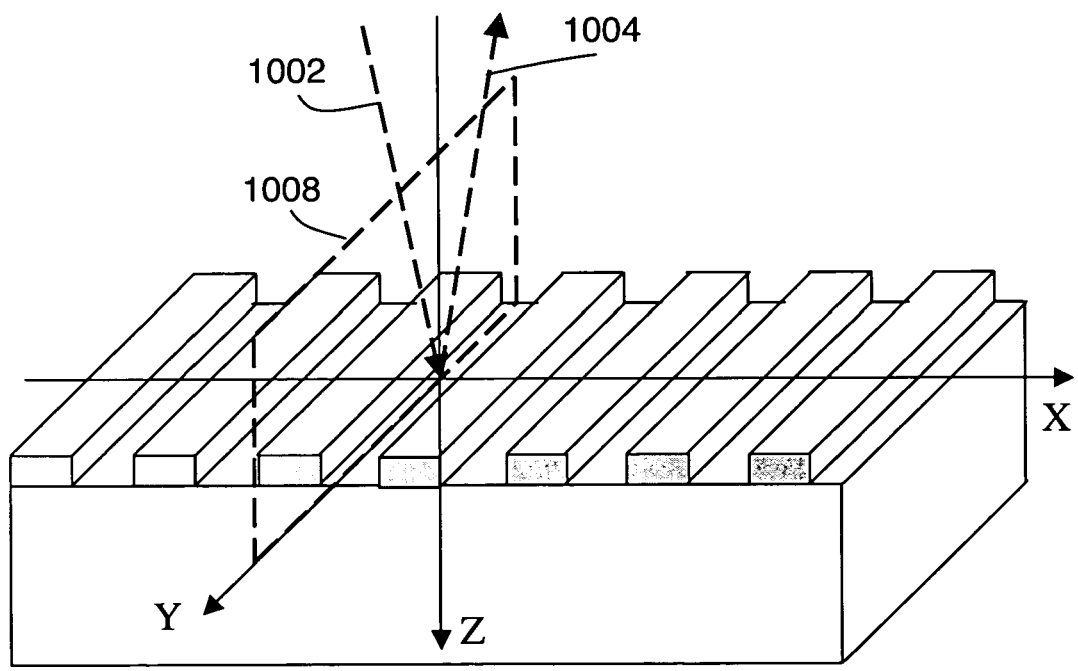
FIG. 10b shows illumination of a grating structure with a plane of incidence parallel to the grating lines.

FIG. 10a shows illumination of a grating structure with a plane of incidence 1006 perpendicular to the grating lines. Plane of incidence 1006 on FIG. 10a contains incident and reflected beam paths 1002 and 1004 respectively. FIG. 10b shows illumination of a grating structure with a plane of incidence 1008 parallel to the grating lines. Plane of incidence 1008 on FIG. 10b contains incident and reflected beam paths 1002 and 1004 respectively.

Figure 11A:
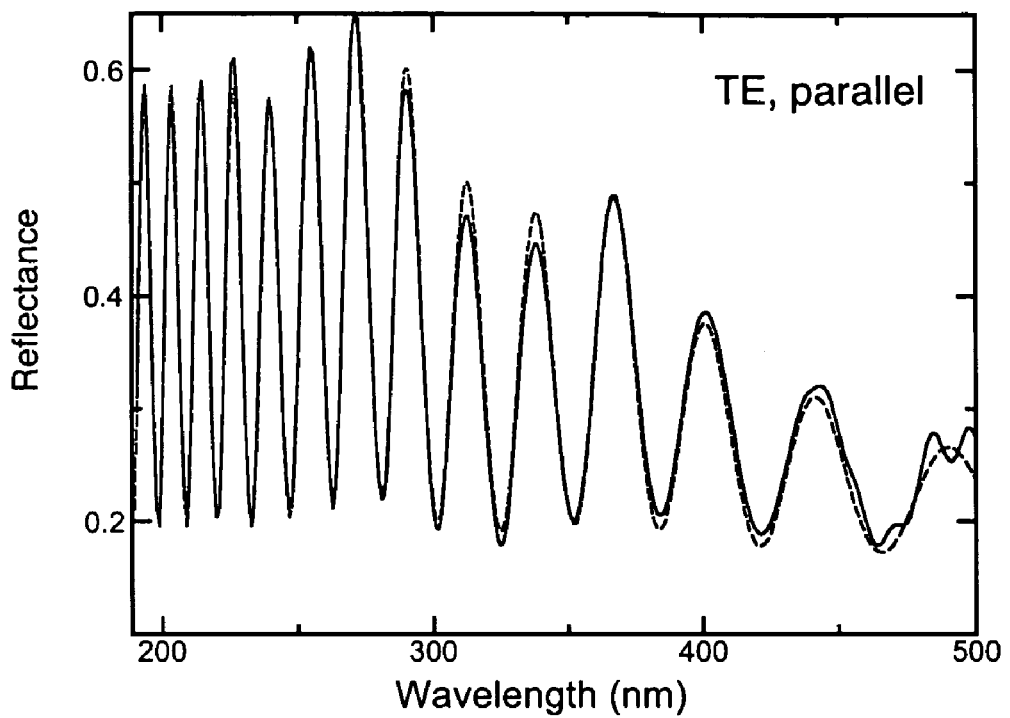
FIGS. 11a–b compare calculated RCWA results to results according to the present invention for a second example (TE polarization).
Figure 11B:
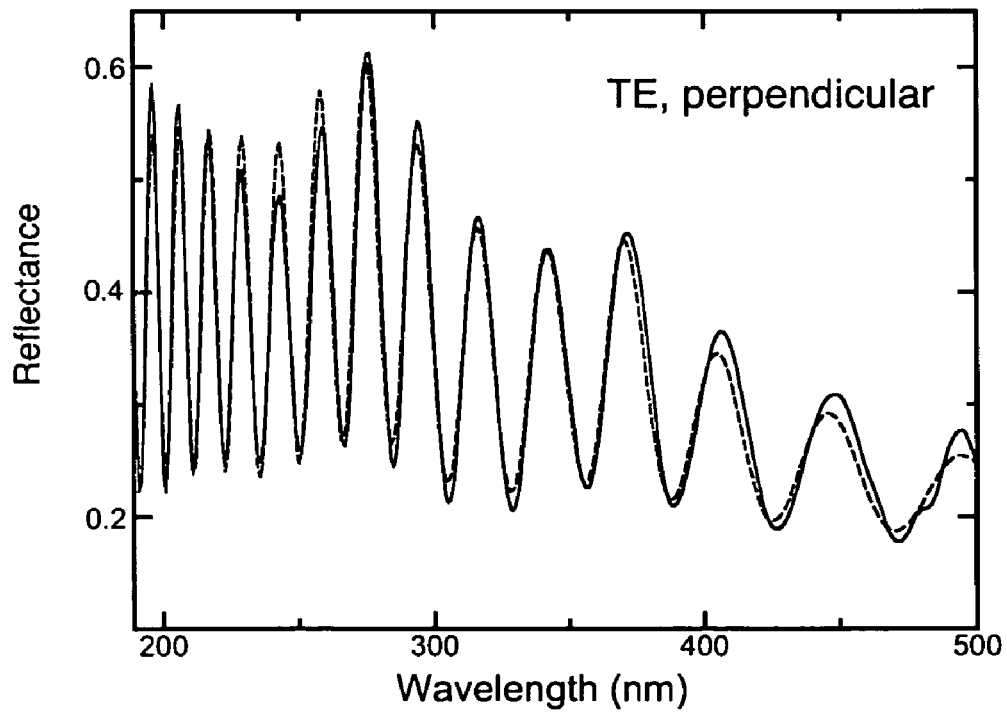
Figure 12A:
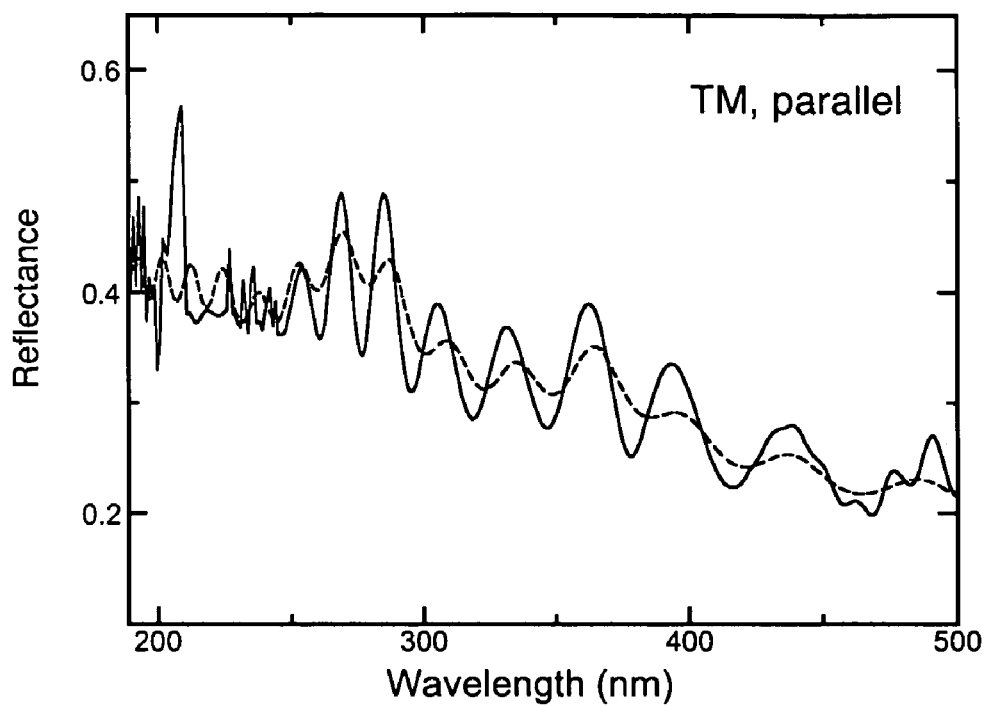
FIGS. 12a–b compare calculated RCWA results to results according to the present invention for the second example (TM polarization).
Figure 12B:
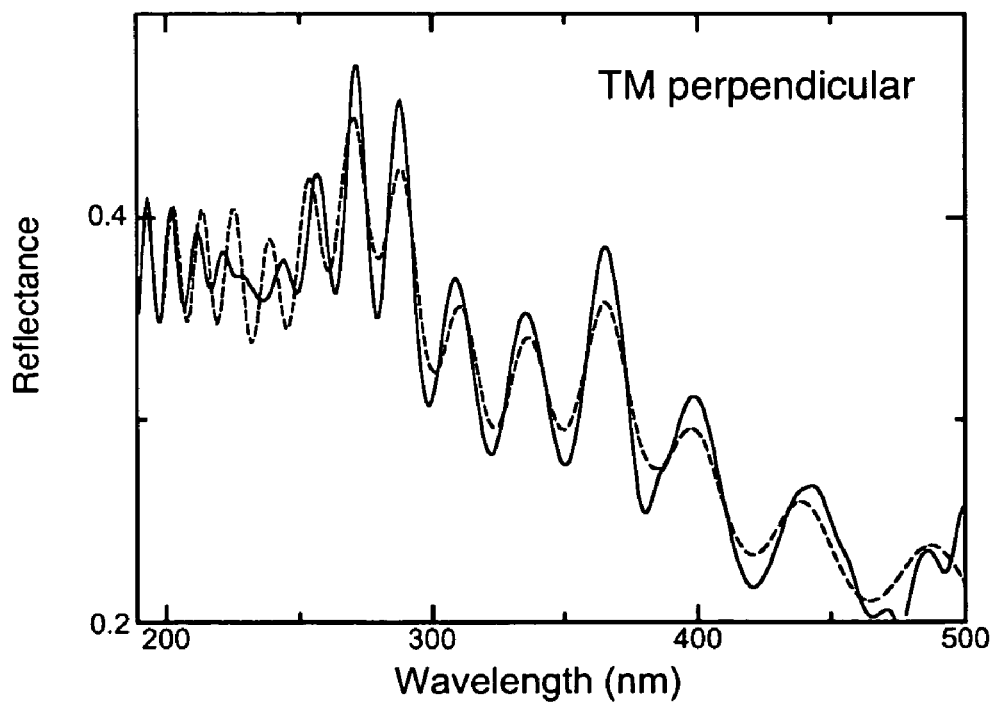

FIGS. 11a–b and 12a–b compare calculated RCWA results to waveguide scalar model results for a second example. In this second example, the angle of incidence is 9°, and the grating has 1.5 µm Si lines and 0.5 µm air trenches (thus Λ=2 µm), and a depth of 2 µm. This grating is on a Si substrate. FIGS. 11a–b show results for TE polarization, and FIGS. 12a–b show results for TM polarization. For FIGS. 11a and 12a, the plane of incidence is parallel to the grating lines (as shown on FIG. 10b), and for FIGS. 11b and 12b, the plane of incidence is perpendicular to the grating lines (as shown on FIG. 10a). The waveguide scalar model results are obtained by curve fitting to match the RCWA results, using trench width, trench areal fraction and depth as independent fitting parameters. Note that here TE and TM polarization refer to the underlying waveguide modes, and not to the plane of incidence. For example, "TE polarized" light on FIG. 10b has an electric field in the plane of incidence (instead of perpendicular to the plane of incidence), since incident light with this polarization excites TE waveguide modes in the lines and trenches of the grating.

Comparison of FIGS. 11a–b with FIGS. 12a–b shows much better agreement between RCWA results and waveguide scalar model results for TE polarization than for TM polarization. Thus TE polarization is preferred. The estimated parameters obtained from the calculation of FIG. 11a are: depth=1.9999 µm, trench width=0.5005 µm, and trench areal fraction=0.222. The estimated parameters obtained from the calculation of FIG. 11b are: depth=2.0183 µm, trench width=0.5249 µm, and trench areal fraction=0.1778. Better parameter estimates are obtained when the plane of incidence is parallel to the grating lines (e.g., FIG. 11a) than when the plane of incidence is perpendicular to the grating lines (e.g., FIG. 11b). For this reason it is preferred, in cases where illumination is not at normal incidence, for the plane of incidence to be parallel to the grating lines. It is also preferable for the angle of incidence to be as small as possible, and more preferably normal incidence illumination is employed. As in the example of FIG. 9c, results for depth and trench width on FIG. 11a are very accurate, while the areal fraction estimate is not so accurate.

Since the scalar waveguide model provides good results for depth and trench width, and less accurate results for trench areal fraction, corrections applicable directly to the trench areal fraction are of greatest interest. Two such corrections have been identified. The first correction can be obtained by accounting for the difference between waveguide mode width and core width, and the second correction can be obtained by considering the effect of geometrical shadowing in a trench. These two corrections will be considered in turn. Results will only be given for TE modes, since illumination with TE polarized light is preferred.

Figure 13A:
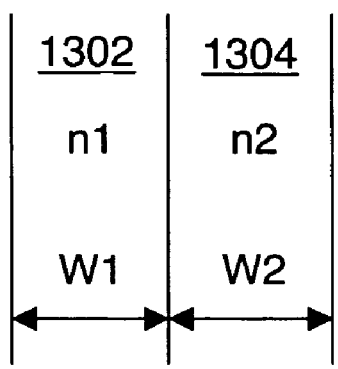
FIGS. 13a and 13b show waveguide modal width for correcting areal fractions in accordance with an embodiment of the invention.
Figure 13B:
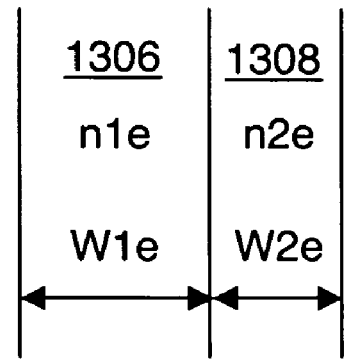

FIG. 13a shows a top view of a unit cell of a grating structure having features 1302 and 1304 with widths W1 and W2 and indices n1 and n2 respectively. FIG. 13b shows a model for the structure of FIG. 13a, where feature 1302 is modeled as a feature 1306 having an effective index n1e and an effective width W1e, and feature 1304 is modeled as a feature 1308 having an effective index n2e and an effective width W2e. When a waveguide analysis is used to calculate n1e and n2e, W1e and W2e (or equivalent width parameters) can be obtained from the pertinent waveguide modal widths.

The effective width of a planar waveguide (i.e., the mode width) is different from the physical width of the waveguide core, as described in various references. For example, in Optical Integrated Circuits, by Hiroshi Nishihara et al, Chapter 2, p. 15, McGraw-Hill Book Company. For a symmetric planar waveguide having a core width W, the modal width $W_{eff}$ is given by $$W_{eff} = W + \frac{2}{\gamma_{cl}}, \quad (1)$$

where $\gamma_{cl}=k\cdot(n^2-n_{cl}^2)/|n^2-n_{cl}^2|^{3/2}$, n is the real part of the effective modal refractive index $n_{eff}$, and $n_{cl}$ is real part of the refractive index of the cladding. For a guided mode, $2/\gamma_{cl}$ accounts for the spread or penetration of the wave into the cladding medium (on both sides). Since refractive indices are wavelength dependent, an average width correction $\Delta W_1$ is computed. The correction $\Delta W_1$ is given by $$\Delta W_1 = \frac{1}{\Delta\lambda}\int_{\lambda_1}^{\lambda_2}\frac{2}{\gamma_{cl}}d\lambda = \frac{1}{\pi\Delta\lambda}\int_{\lambda_1}^{\lambda_2}\frac{(n^2-n_{cl}^2)\lambda\cdot d\lambda}{|n^2-n_{cl}^2|^{3/2}}, \quad (2)$$

where $\Delta\lambda=\lambda_2-\lambda_1$ is the wavelength range for the curve fit. Eqs. 1 and 2 are applicable to both guided modes (where $\Delta W_1$ is positive) and leaky modes (where $\Delta W_1$ is negative).

The width correction of Eqs. 1 and 2 is preferably used to correct estimated trench areal fraction in the scalar waveguide model as follows. Let W and f be the trench width and trench areal fraction estimates, respectively, provided by a waveguide scalar model curve fit. A corrected trench areal fraction f* is given by $$f^* = f\left(1-\frac{\Delta W_1}{W}\right), \quad (3)$$

where the correction $\Delta W_1$ is given by Eq. 2.

When the correction of Eqs. 2 and 3 is applied to the example of FIG. 9c, the estimated trench areal fraction is changed from f=0.164 to f*=0.195, which is much closer to the true trench areal fraction of 0.2 in this example. Similarly, application of the correction of Eqs. 2 and 3 to the example of FIG. 11a changes the estimated trench areal fraction from f=0.222 to f*=0.253, which is much closer to the true trench areal fraction of 0.25 in this example. Note that the correction of Eqs. 2 and 3 can be applied after the curve fitting of the waveguide scalar model is performed (i.e., this correction does not require additional computation during curve fitting). Thus, the extra computation time required to implement this correction is typically negligible.

The correction of Eqs. 2 and 3 can also be used to provide a correction to the trench width in addition to providing a correction to the trench areal fraction. Such a width correction is particularly useful in cases where the waveguide modal refractive index does not differ greatly from the core material intrinsic refractive index, since in such cases, the core width estimate provided by an uncorrected waveguide scalar model tends to be less reliable. For example, if the trench width and grating pitch in the example of FIG. 9c are changed to 1 µm and 3 µm respectively, then the estimated trench width W=0.970 µm and the estimated corrected areal fraction f*=0.326. The corresponding corrected trench width W*=W(f*/f) is 0.978 µm, which is closer to the true value of 1 µm than W.

Figure 14:
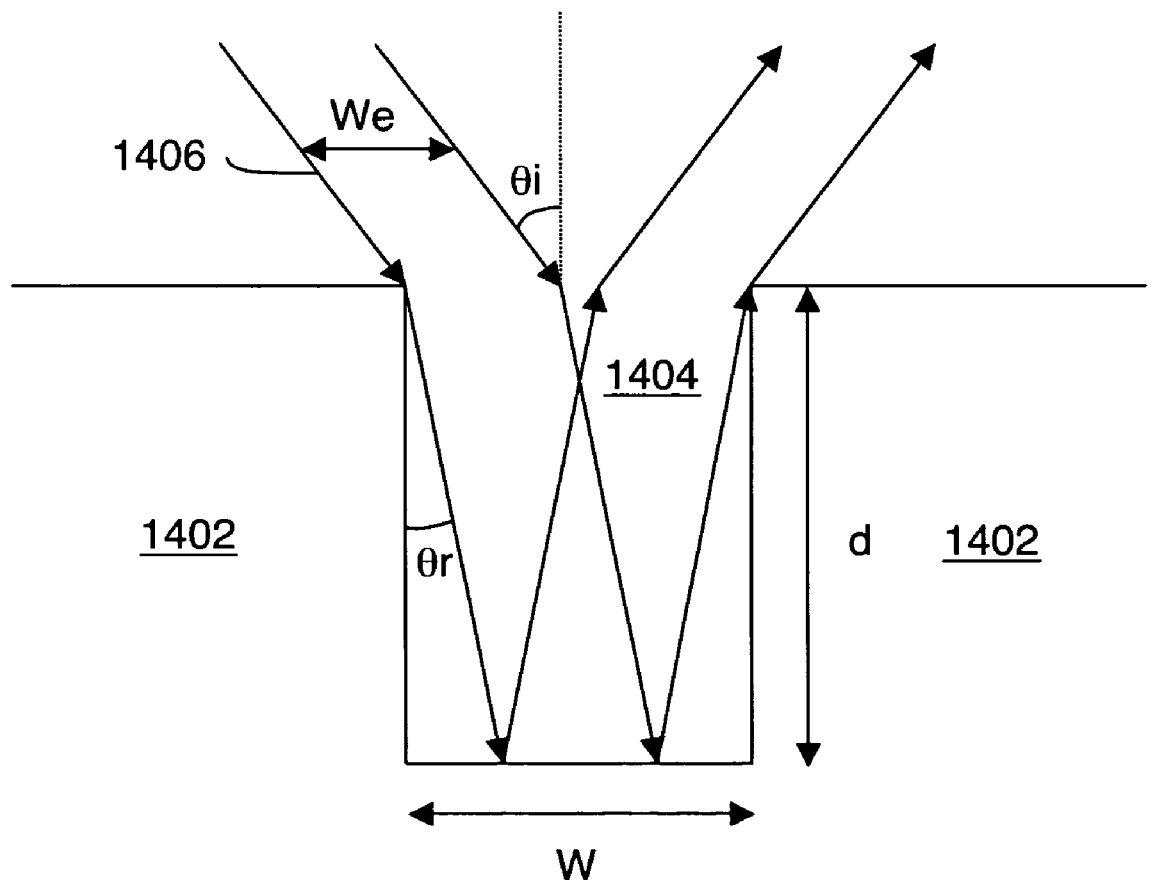
FIG. 14 shows geometry for calculating a correction to trench width for shadowing according to an embodiment of the invention.

FIG. 14 shows geometry relating to correcting an estimated areal fraction to account for shadowing in a trench 1404 surrounded by walls 1402. Shadowing in a trench occurs only if the plane of incidence is perpendicular to the grating lines (as in FIG. 10a). Thus, a shadowing correction is not made if the plane of incidence is parallel to the grating lines (as in FIG. 10b). If the trench dimensions W and d on FIG. 14 are large compared to a wavelength, the geometrical shadowing effect is straightforward. The physical trench width W would be replaced by We, which can be calculated in a straightforward way from Snell's law and the geometry of FIG. 14. However, the cases of interest here relate to trench dimensions on the order of a wavelength, or smaller, and thus the shadowing correction becomes more complicated.

It is helpful to define an effective propagation angle $\theta_e$ for light propagating in the trench waveguide mode, which is given by $$\theta_e=\cos^{-1}[Re(n_e)/Re(n_{co})], \quad (4)$$

where $n_e$ is the modal effective refractive index, and $n_{co}$ is the intrinsic refractive index of the trench material. Frequently, $n_{co}=1$ (e.g., for an air trench). Since curve fitting is performed over a range of wavelengths, the minimum and maximum values of $\theta_e$ over the relevant wavelength range are defined as $\theta_1$ and $\theta_2$ respectively. The geometrical refraction angle $\theta_r$ is given by $$\theta_r=\sin^{-1}[Re(n_i)\sin\theta_e/Re(n_e)], \quad (5)$$

where $n_i$ is the refractive index of the incident medium (frequently $n_i=1.0$ for incidence from air), and $\theta_i$ is the angle of incidence of a light beam 1406. The wavelength dependence of $\theta_r$ is accounted for in the wavelength averaging of Eq. 14 below.

The following calculations relate to leaky modes, since the trench waveguide mode is typically a leaky mode. The shadowing correction for a guided mode is the negative of the leaky mode shadowing correction. Three cases are distinguished, based on the trench aspect ratio.

Case 1: $d*\tan\theta_r < W/2$:

The shadowing correction, $\Delta W_2$, for the waveguide width in this case is given by:

$$\Delta W_2 = -2d \tan\theta_r + \delta_1 + \delta_2 \cdot \alpha. \quad (6)$$

Here $\alpha = \exp(-4\pi \cdot n_{imag} \cdot d/\lambda)$ accounts for attenuation, where $n_{imag}$ is the imaginary part of the effective modal refractive index, $\delta_1$ is given by $$\delta_1 = \begin{cases} d(\tan\theta_r - \tan\theta_1) \cdot \frac{\theta_r - \theta_1}{\theta_2 - \theta_1}, & \theta_1 < \theta_r \\ 0, & \theta_1 \geq \theta_r, \end{cases} \quad (7)$$

and $\delta_2$ is given by $$\delta_2 = \begin{cases} (2d\tan\theta_2 - W) \cdot \frac{\theta_2 - \theta_{10}}{\theta_2 - \theta_1} & W/2 < d\tan\theta_2 < W \\ W \frac{\theta_2 - \theta_{10}}{\theta_2 - \theta_1} & d\tan\theta_2 > W \\ 0 & d\tan\theta_2 < W/2, \end{cases} \quad (8)$$

where $\theta_{10} = \tan^{-1}(W/2d)$.

In Eq. 6, $2d \tan\theta_r$ is the width of the geometrical shadowing area from ray optics. Corrections are added to this term to account for waveguide effects. $\delta_1$ and $\delta_2$ are the correction terms to the shadowing area from small ($\theta_1 < \theta_e < \theta_r$) and large ($\theta_r < \theta_e < \theta_2$) effective propagation angles, respectively. The quantities $d(\tan\theta_r - \tan\theta_1)$ and $(2d \tan\theta_2 - W)$ are the widths in which waves with small and large effective propagation angles can contribute to the reflection in the measurement, respectively. The quantities $(\theta_r - \theta_1)/(\theta_2 - \theta_1)$ and $(\theta_2 - \theta_{10})/(\theta_2 - \theta_1)$ are the fractions of small and large effective propagation angles, respectively, within the whole range of effective propagation angles. When $d \tan\theta_2 > W$, the correction from large effective propagation angles will cover the whole width of the waveguide. For large effective propagation angles, $\alpha$ is introduced to account for attenuation in waveguide propagation.

Case 2: $W/2 < d*\tan\theta_r < W$:

The shadowing correction, $\Delta W_2$, for the waveguide width in this case is given by:

$$\Delta W_2 = -W + (2d \tan\theta_r - W) \cdot \alpha + \delta_1 + \delta_2 \cdot \alpha \quad (9)$$

Here $$\delta_1 = \begin{cases} (W - d\tan\theta_1) \cdot \frac{\theta_{10} - \theta_1}{\theta_2 - \theta_1} & \theta_1 < \theta_r, \; d\tan\theta_1 < \frac{W}{2} \\ 0 & \text{else}, \end{cases} \quad (10)$$

$$\delta_2 = \begin{cases} (3W - 2D_2) \cdot \frac{\theta_2 - \theta_{20}}{\theta_2 - \theta_1} & D_2 > W \\ 0 & D_2 < W, \end{cases} \quad (11)$$

$D_2 = \min\{1.5W, d \tan\theta_2\}$, and $\theta_{20} = \tan^{-1}(W/d)$.

For this case, the geometrical shadowing area is W (i.e., the whole width of the trench). Three extra terms are added to take waveguiding into account. The quantity $(2d \tan\theta_2 - W)$ is the correction to the shadowing area from multiple reflections. The quantities $\delta_1$ and $\delta_2$ are the corrections from small and large effective propagation angles, respectively. The quantities $(W - d \tan\theta_1)$ and $(3W - 2D_2)$ are the widths in which waves with small and large effective propagation angles can contribute to the reflection. The attenuation $\alpha$ is included for large effective propagation angles that undergo multiple reflections.

Case 3: $d*\tan\theta_r > W$:

For this case, there is no shadowing correction, i.e., $$\Delta W_2 = 0. \quad (12)$$

The shadowing correction $\Delta W_2$ given by Eqs. 6, 9, and/or 12 can be wavelength-dependent, and in such cases wavelength averaging of $\Delta W_2$ over the relevant wavelength range is preferably performed. Once a suitably wavelength-averaged $\Delta W_2$ is computed, it can be used in addition to or instead of the modal width correction in Eq. 3 (i.e., $\Delta W_1$ in Eq. 3 can be replaced by $\Delta W_2$ or by $\Delta W_1 + \Delta W_2$) to compute an improved areal fraction estimate f*.

Alternatively, a single combined average correction factor $\Delta W$ can be computed as follows. A wavelength dependent weight function $g(\lambda)$ is defined by $$g(\lambda) = \exp\left[-\frac{\lambda \cdot (d - a_t \cdot W)}{W^2}\right], \quad (13)$$

where $a_t$ is an averaging parameter that is empirically adjusted to provide the most accurate fitting results. The parameter $a_t$ provided by such empirical adjustment has a weak dependence on d and W ($a_t$ increases as d increases, and decreases as W increases), but the total variation is not large (i.e., it is within +/−50% or so). In practice, $a_t \approx 0.1$ has been found suitable. Combining the waveguide ($\Delta W_1$) and shadowing ($\Delta W_2$) effects, an average width correction, valid for both guided and leaky modes, is given by $$\Delta W = \quad (14)$$

$$\begin{cases} \frac{1}{\Delta\lambda} \int_{\lambda_1}^{\lambda_2} \left\{ \frac{[1 - g(\lambda)]\lambda}{\pi\sqrt{n^2 - n_c^2}} - g(\lambda) \cdot \Delta W_2 \right\} \cdot \frac{n^2 - n_c^2}{|n^2 - n_c^2|} d\lambda & d\tan\theta_r \leq W \\ \frac{1}{\pi\Delta\lambda} \int_{\lambda_1}^{\lambda_2} \frac{\lambda \cdot (n^2 - n_c^2) d\lambda}{|n^2 - n_c^2|^{3/2}} & d\tan\theta_r > W \end{cases}$$

The width correction $\Delta W$ given by Eq. 14 can be used instead of $\Delta W_1$ in Eq. 3 to compute an improved estimate for areal fraction. When the incident plane is parallel to the trench/grating lines, there is no shadowing effect and Eq. 2 should be used instead of Eq. 14.

We apply the correction of Eq. 14 to an example. This example is a grating, with pitch=4 µm, depth=2 µm, and having Si line width=3 µm and trench (air) line width=1 µm. The incidence angle is 4°, the plane of incidence is perpendicular to the grating lines, and polarization is TE relative to the pertinent waveguide modes. The parameter estimates from the waveguide based scalar model are: trench depth=2.002 µm, trench width=1.0655 µm, and trench areal fraction f=0.18. Applications of Eqs. 14 and 3 provides an improved areal fraction estimate of f*=0.21, which is closer to the true value of 0.25 in this example.

The preceding description of embodiments of the invention has been by way of example, and not limitation. Accordingly, the invention can be practiced with many modifications of the above described details.

Figure 15:
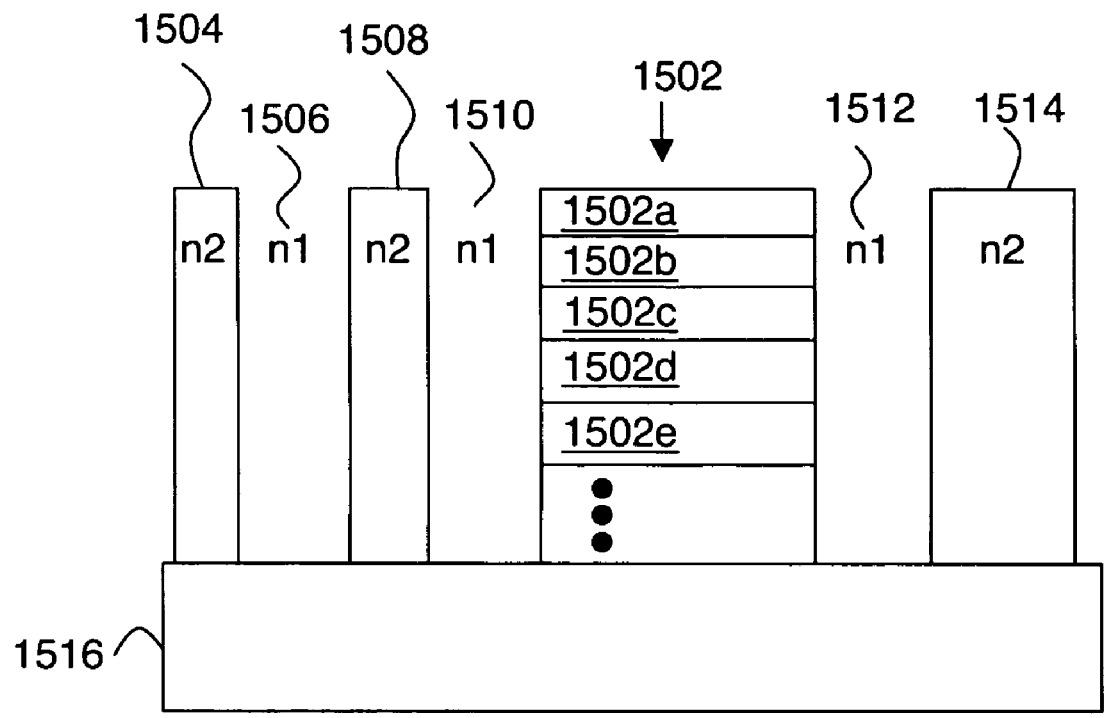
FIG. 15 shows use of an effective medium refractive index according to an embodiment of the invention.

For example, as shown on FIG. 15, an embodiment of the invention can make use of an effective optical property other than a waveguide modal refractive index to improve a scalar model calculation. In the example of FIG. 15, a grating structure on a substrate 1516 has lines 1504, 1508, and 1514 having refractive index n2, and trenches 1506, 1510, and 1512 having refractive index n1. The grating structure includes a multilayer lines 1502 having layers 1502a, 1502b etc. An effective medium approximation, as known in the art, can be used to compute an effective refractive index n3e of multilayer 1502. Such an effective index approximation is reasonably accurate if each individual layer has a thickness substantially less than the incident light wavelength. The effective index n3e will depend on the geometry of multilayer 1502 (i.e., the layer thicknesses), and on intrinsic material optical properties (i.e., the layer indices). The effective index n3e can be used in a scalar model computation of the reflectance of the pattern of FIG. 15. Such a computation can be done in significantly less time than a computation that explicitly accounts for every layer within multilayer 1502.

Figure 16:
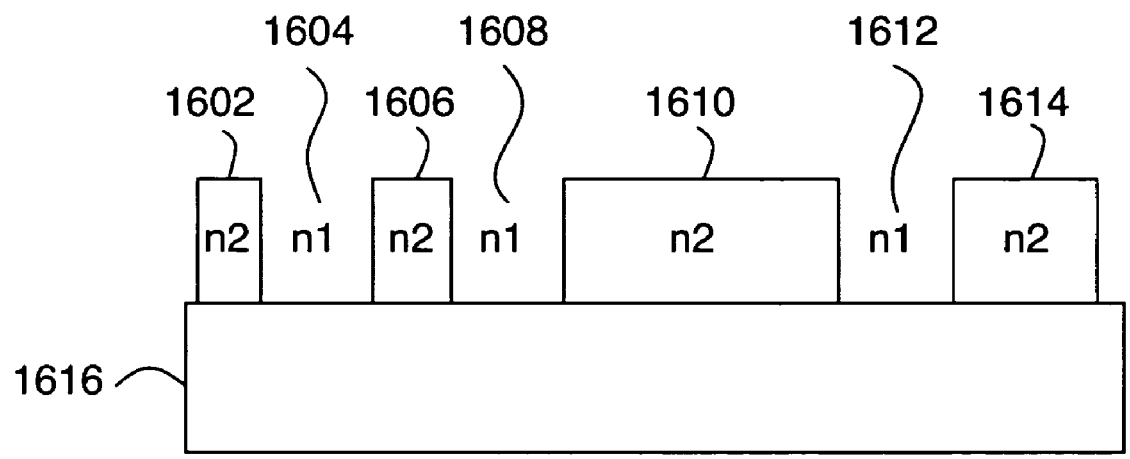
FIG. 16 shows a side view of a one-dimensional non-periodic structure which can be characterized according to the invention.

Another example of an alternate embodiment of the invention is shown on FIG. 16, where a structure on a substrate 1616 has lines 1602, 1606, 1610, and 1614 separated by trenches 1604, 1608, and 1612. The spacing between any two adjacent trenches is not the same throughout the structure, so it is not periodic. The present invention is applicable to characterization of such a non-periodic structure. Note that some commonly used calculation approaches, such as the RCWA, are inapplicable to non-periodic structures.

Figure 17:
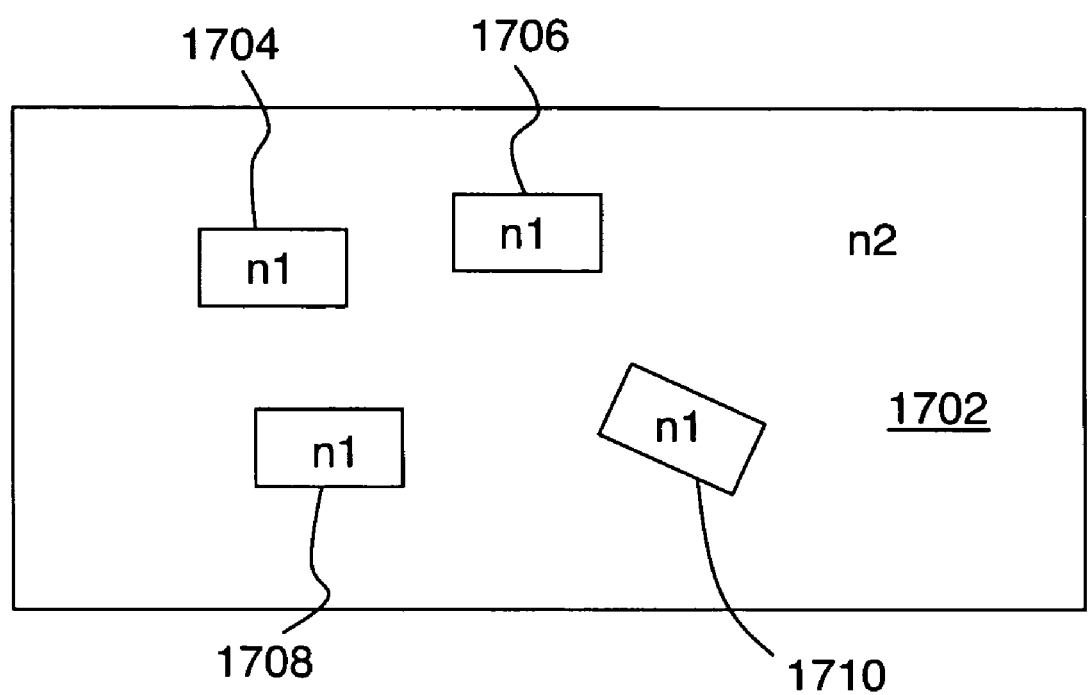
FIG. 17 shows a top view of a two-dimensional patterned structure which can be characterized according to the invention.

Yet another structure which can be optically characterized according to the invention is shown on FIG. 17, which is a top view of a two-dimensional pattern having features 1704, 1706, 1708, and 1710 having refractive index n1 surrounded by a background 1702 having refractive index n2. An effective index n1e can be computed for the two-dimensional waveguides having core with index n1 surrounded by a cladding with index n2. The effective index n1e can be used to improve a scalar model calculation of the properties of the pattern of FIG. 17. Since the background region 1702 in this example does not really act as a waveguide core, its intrinsic refractive index is used without modification in the scalar model calculations.

The preceding examples relate to measuring and modeling reflectance (into the zeroth diffraction order). Characterization according to the invention can also be done by measuring and modeling transmittance (into the zeroth diffraction order). Furthermore, in the preceding grating examples, effective indices were used for both the lines and the trenches. In some cases, either the lines or the trenches are large enough to render waveguide corrections negligible, and in such cases, computation time can be reduced by only calculating effective indices for features having non-negligible waveguide corrections. In other words, there is no need to use effective indices for all features of a particular pattern. For simplicity, the preceding examples relate to patterns having two kinds of features (e.g., lines and trenches). The invention is also applicable to patterns having three or more kinds of features (e.g., a trench and 2 lines having different widths), and the number of fitting parameters will correspondingly increase.

In some cases, the fit between modeled and measured results can be improved by multiplying modeled results with an empirical loss factor to account for light lost to scattering and/or diffraction. Such a loss factor $L(\lambda)$ can take various forms, such as $L(\lambda)=A+B\lambda+C\lambda^2$ or $L(\lambda)=A+\exp(B\lambda^2)$, where A, B and C are parameters to be empirically determined. In many cases, a fixed loss factor (i.e., only using the A parameter) is sufficient.

Appendix A—Symmetric Planar Waveguides

Procedures for solving the dispersion equations for guided and leaky modes in symmetric planar waveguides are described here in detail.

A z-propagating electromagnetic wave in a y-invariant and z-invariant region (e.g., within the region of lines 104 and trenches 106 on FIG. 1a) can be written as (refer to Fundamentals of Optical Waveguides, by Katsunari Okamoto, Chapter 2, Academic Press):

$$\vec{E} = \vec{E}(x)\exp[j(\omega t - \beta z)]$$

$$\vec{H} = \vec{H}(x)\exp[j(\omega t - \beta z)] \tag{A1}$$

Here $\beta$ is the propagation constant to be determined from Maxwell's equations. The effective modal refractive index ($n_{eff}$) is given by:

$$n_{eff} = \frac{\beta}{k}, \tag{A2}$$

where the wave number $k=2\pi/\lambda$, and $\lambda$ is the vacuum wavelength of the incident light.

For planar waveguides, TE and TM modes can be treated separately. The electric field vector of the TE mode is in the y direction on FIG. 1a, while the magnetic field vector of the TM mode is in the y direction on FIG. 1a.

I. TE Mode

In this case, the electromagnetic field has three components, $E_y$, $H_x$ and $H_z$. A core medium with width 2a=W and complex refractive index $n_1$ is sandwiched by cladding media with complex refractive index $n_2$.

The waveguide equations, which are derived from Maxwell equations, are $$\frac{d^2 E_y}{dx^2} + (k^2 n^2 - \beta^2)E_y = 0, \tag{A3}$$

$$H_x = -\frac{\beta}{\omega\mu_0}E_y,$$

$$H_z = \frac{j}{\omega\mu_0}\frac{dE_y}{dx}.$$

Ignoring the dependence on t and z in Eq. A1, solutions to the above equations can be written as:

$$E_y = \qquad (A4)$$

$$\begin{cases} \cos(Ka-\phi)\{A_1\exp[\sigma(x-a)]+A_2\exp[-\sigma(x-a)]\} & x>a \\ \cos(Kx-\phi) & -a<x<a \\ \cos(Ka+\phi)\{B_1\exp[\sigma(x+a)]+B_2\exp[-\sigma(x+a)]\} & x<-a. \end{cases}$$

Here $\phi$ is an arbitrary constant, and $A_1$, $A_2$, $B_1$, and $B_2$ are coefficients to be determined by imposition of boundary conditions. K and $\sigma$ are wave numbers along the x-axis in the core and cladding regions, respectively, $$K = \sqrt{k^2 n_1^2 - \beta^2} \qquad (A5)$$

$$\sigma = \sqrt{\beta^2 - k^2 n_2^2},$$

$$K^2 + \sigma^2 = k^2(n_1^2 - n_2^2). \qquad (A6)$$

Imposition of boundary conditions at x=±a yields $$A_1 = \frac{1}{2}\left[1 - \frac{K}{\sigma}\tan(Ka-\phi)\right] \qquad (A7)$$

$$A_2 = \frac{1}{2}\left[1 + \frac{K}{\sigma}\tan(Ka-\phi)\right]$$

$$B_1 = \frac{1}{2}\left[1 + \frac{K}{\sigma}\tan(Ka+\phi)\right]$$

$$B_2 = \frac{1}{2}\left[1 - \frac{K}{\sigma}\tan(Ka+\phi)\right].$$

We classify the waveguide modes into several cases, and give a stable solution for each case.

A. Guided TE Mode:

This is the case when the real part of $\sigma$ is positive or zero. It requires $A_1=B_2=0$ in order to keep $E_y$ in Eq. A4 finite. Here we treat two situations separately.

(1) real($\sigma/K$)>=0:

From Eq. A7 and $A_1=B_2=0$, one can obtain $$Ka = \frac{m\pi}{2} + \tan^{-1}\left(\frac{\sigma}{K}\right) \qquad (A8)$$

where m (=0, 1, 2, . . . ) is the mode number.

(2) real($\sigma/K$)<0:

Eq. A8 can be re-written as $$\begin{cases} Ka = \frac{m\pi}{2} + \cos^{-1}\left(\frac{\sqrt[k]{n_1^2-n_2^2}}{\sigma a}\right) & 0<Q<\pi/2 \\ Ka = \frac{(m+2)\pi}{2} + \cos^{-1}\left(\frac{\sqrt[k]{n_1^2-n_2^2}}{\sigma a}\right) & -\pi/2<Q<0 \end{cases} \qquad (A9)$$

where $$Q = \text{real}\left[\tan^{-1}\left(\frac{\sigma}{K}\right)\right].$$

]. Eq. A9 is more numerically stable than Eq. A8 for this case.

B. Leaky TE Mode:

This is the case when the real part of $\sigma$ is negative. It requires $A_2=B_1=0$ to keep $E_y$ finite. Combining this with Eq. A7, we have $$Ka = \frac{m\pi}{2} + \tan^{-1}\left(-\frac{\sigma}{K}\right) \qquad (A10)$$

Eq. A8, A9, or A10 can be combined with Eq. A6 to solve for K and $\sigma$ using, for example, the Newton-Raphson method and/or conjugate gradient methods (Numerical Recipes, (FORTRAN Version), by William H. Press et al., Cambridge University Press, p. 269, p. 301, 1989). Once K is obtained, the effective modal refractive index $n_{\text{eff}}$ can be obtained from Eqs. A2 and A5.

II. TM Mode

Similar to Eq. (A4), the magnetic field also takes the form $$H_y = \begin{cases} \cos(Ka-\phi)\{A_1\exp[\sigma(x-a)]+A_2\exp[-\sigma(x-a)]\} & x>a \\ \cos(Ka-\phi) & -a<x<a \\ \cos(Ka+\phi)\{B_1\exp[\sigma(x+a)]+B_2\exp[-\sigma(x+a)]\} & x<-a \end{cases}$$

Now, the boundary condition at x=±a is:

$$\frac{1}{n_1^2}\frac{\partial H_{y1}}{\partial x} = \frac{1}{n_2^2}\frac{\partial H_{y2}}{\partial x}, \qquad (A11)$$

which yields $$A_1 = \frac{1}{2}\left[1 - \frac{n_2^2 K}{n_1^2 \sigma}\tan(Ka-\phi)\right] \qquad (A12)$$

$$A_2 = \frac{1}{2}\left[1 + \frac{n_2^2 K}{n_1^2 \sigma}\tan(Ka-\phi)\right]$$

$$B_1 = \frac{1}{2}\left[1 + \frac{n_2^2 K}{n_1^2 \sigma}\tan(Ka+\phi)\right]$$

-continued $$B_2 = \frac{1}{2}\left[1 - \frac{n_2^2 K}{n_1^2 \sigma}\tan(Ka + \phi)\right]$$

The stable solutions are given for each case as follows.

A. Guided TM Mode:

This is the case when the real part of σ is positive or zero. It requires $A_1=B_2=0$ to keep $H_y$ finite. Here we treat lossy (the imaginary part of complex $n_1$ is positive or the real part of complex $n_1$ is less than the real part of $n_2$) and lossless (otherwise) modes separately.

(1) Lossless Mode:

$$Ka = \frac{m\pi}{2} + \tan^{-1}\left(\frac{n_1^2 \sigma}{n_2^2 K}\right). \quad (A13)$$

(2) Lossy Mode:

Equation A13 can be rewritten as:

$$Ka = -\frac{n_2^2}{n_1^2}\sigma \cdot a \cdot \tan\left(Ka - \frac{m}{2}\pi\right). \quad (A14)$$

Equation A14 provides improved numerical stability compared to equation A13 when solving for lossy modes.

B. Leaky TM Mode ($\sigma_r < 0$)

This is the case when the real part of σ is negative. It requires $A_2=B_1=0$ to keep $H_y$ finite. Combining this with Eq. A12, we have $$Ka = \frac{m\pi}{2} + \tan^{-1}\left(-\frac{n_1^2 \sigma}{n_2^2 K}\right). \quad (A15)$$

As for the TE mode, Eqs. A13, A14, or A15 can be combined with Eq. A6 to obtain K and σ, and then $n_{\mathit{eff}}$ follows from Eqs. A2 and A5.

If one of the media in a waveguide is a perfect conductor, the electromagnetic wave can only exist in the region sandwiched by the conductor. Using $A_1=A_2=B_1=B_2=0$, Eq. A4 (TE mode) can be rewritten as $$E_y = \begin{cases} \cos(Kx - \phi) & -a < x < a \\ 0 & \text{else} \end{cases} \quad (A16)$$

The boundary conditions at $x=\pm a$ result in $Ka=m\pi/2$ and $\phi=0$. Finally, the dispersion equation can be found from Eqs. A2 and A5 as $$n_{\mathit{eff}} = \frac{\beta}{k} = \sqrt{n_1^2 - \left(\frac{m\lambda}{2W}\right)^2}. \quad (A17)$$

Here m=1 is the main (lowest) mode. This clearly shows that $n_{\mathit{eff}}$ can be significantly different from the intrinsic index $n_1$, especially when the width W of the core is comparable with the wavelength. The cutoff wavelength for TE mode (the longest wavelength that can propagate) is $2Wn_1$.

Similarly, the effective complex refractive index $n_{\mathit{eff}}$ can be calculated for an asymmetric planar waveguide in which the cladding materials on each side are different, or for two dimensional waveguides, such as rectangular waveguides and circular waveguides. These kinds of waveguides are described in the literature, e.g., in Fundamentals of Optical Waveguides, by Katsunari Okamoto, Chapter 2, Academic Press; and in Electromagnetic Wave Theory, by Jin Au Kong, Chapter 3, $2^{nd}$ edition, John Wiley & Sons, Inc.

What is claimed is:

1. A method for optically determining one or more parameters of a pattern having lateral features, each feature having a feature geometry and including materials having intrinsic optical properties, the method comprising:
   a) illuminating said pattern with optical radiation;
   b) measuring a measured pattern response by collecting radiation from said illuminated pattern;
   c) calculating a feature plane-wave response from each of said features, wherein at least one of said plane-wave responses depends on at least one effective optical property dependent on said feature geometry and said intrinsic optical properties;
   d) combining said feature plane-wave responses to provide a modeled pattern response having said one or more parameters as variables; and
   e) determining said one or more parameters by adjusting said variables to fit said modeled pattern response to said measured pattern response.

2. The method of claim 1, wherein said effective optical property comprises a real or complex waveguide modal refractive index.

3. The method of claim 2, wherein said combining is according to areal fraction of each of said features, and wherein said combining further comprises use of a waveguide modal width to correct at least one of said areal fractions.

4. The method of claim 2, wherein said waveguide modal refractive index relates to a symmetric planar waveguide.

5. The method of claim 4, wherein said waveguide modal refractive index is $n_e$, wherein said symmetric planar waveguide has a core width of 2a, a complex core index of $n_1$ and a complex cladding index of $n_2$, wherein λ is a free space optical wavelength, $k=2\pi/\lambda$, $\beta=kn_e$, $K=\sqrt{k^2 n_1^2 - \beta^2}$, $\sigma=\sqrt{\beta^2 - k^2 n_2^2}$, $$Q = Re\left\{\tan^{-1}\left(\frac{\sigma}{K}\right)\right\},$$

and a mode number m is a non-negative integer, and wherein the method further comprises finding guided TE modes by numerically solving:

$$Ka = \frac{m\pi}{2} + \tan^{-1}\left(\frac{\sigma}{K}\right)$$

if Re(σ/K)≧0, $$Ka = \frac{m\pi}{2} + \cos^{-1}\left(\frac{\sqrt[k]{n_1^2 - n_2^2}}{\sigma a}\right)$$

if Re(σ/K)<0 and 0<Q<π/2, $$Ka = \frac{(m+2)\pi}{2} + \cos^{-1}\left(\frac{\sqrt[k]{n_1^2 - n_2^2}}{\sigma a}\right)$$

if Re(σ/K)<0 and −π/2<Q<0.

6. The method of claim 4, wherein said waveguide modal refractive index is $n_e$, wherein said symmetric planar waveguide has a core width of 2a, a complex core index of $n_1$ and a complex cladding index of $n_2$, wherein λ is a free space optical wavelength, $k=2\pi/\lambda$, $\beta=kn_e$, $K=\sqrt{k^2n_1^2-\beta^2}$, $\sigma=\sqrt{\beta^2-k^2n_2^2}$, $$Q = Re\left\{\tan^{-1}\left(\frac{\sigma}{K}\right)\right\},$$

and a mode number m is a non-negative integer, and wherein the method further comprises finding guided TM modes by numerically solving:

$$Ka = \frac{m\pi}{2} + \tan^{-1}\left(\frac{\sigma n_1^2}{Kn_2^2}\right)$$

if Im(n1)>0 or Re(n1)<Re(n2), $$Ka = -\frac{\sigma a n_2^2}{n_1^2}\tan\left(Ka - \frac{m\pi}{2}\right)$$

if Im(n1)=0 and Re(n1)≧Re(n2).

7. The method of claim 1, wherein said effective optical property comprises a real or complex effective medium refractive index.

8. The method of claim 1, wherein said combining is coherent, incoherent, or partially coherent.

9. The method of claim 1, wherein said combining is according to areal fraction of each of said features.

10. The method of claim 1, further comprising providing a loss factor in said modeled pattern response.

11. A system for optically determining one or more parameters of a pattern having lateral features, each feature having a feature geometry and including materials having intrinsic optical properties, the system comprising:
 a) an optical source for illuminating said pattern with optical radiation;
 b) an optical detector for measuring a measured pattern response by collecting radiation from said illuminated pattern; and
 c) a processor for:
  i) calculating a feature plane-wave response from each of said features, wherein at least one of said plane-wave responses depends on at least one effective optical property dependent on said feature geometry and said intrinsic optical properties; and
  ii) combining said feature plane-wave responses to provide a modeled pattern response having said one or more parameters as variables;
 wherein said one or more parameters are determined by said processor by adjusting said variables to fit said modeled pattern response to said measured pattern response.

12. The system of claim 11, wherein said parameters are selected from the group consisting of a feature width, a feature length, a feature area, a feature depth, a feature real refractive index and a feature complex refractive index.

13. The system of claim 11, wherein said measured pattern response is a measured pattern reflectance and said modeled pattern response is a modeled pattern reflectance.

14. The system of claim 11, wherein said measured pattern response is a measured pattern transmittance and said modeled pattern response is a modeled pattern transmittance.

15. The system of claim 11, wherein said measured pattern response is a measured spectral pattern response and said modeled pattern response is a modeled spectral pattern response.

16. The system of claim 11, wherein said effective optical property comprises a real or complex waveguide modal refractive index.

17. The system of claim 16, wherein said optical radiation is substantially TE polarized with respect to a waveguide corresponding to said waveguide modal refractive index.

18. The system of claim 16, wherein said combining is according to areal fraction of each of said features, and wherein said combining further comprises use of a waveguide modal width to correct at least one of said areal fractions.

19. The system of claim 11, wherein said effective optical property comprises a real or complex effective medium refractive index.

20. The system of claim 11, wherein said features are substantially periodic.

21. The system of claim 11, wherein said features are substantially non-periodic.

22. The system of claim 11, wherein said features substantially vary one-dimensionally, thereby forming a grating having lines.

23. The system of claim 22, wherein a plane of incidence of said optical radiation is parallel to said lines.

24. The system of claim 22, wherein a plane of incidence of said optical radiation is perpendicular to said lines.

25. The system of claim 24, wherein said combining further comprises correcting a trench width of said grating to account for shadowing.

26. The system of claim 11, wherein said features substantially vary two-dimensionally.

27. The system of claim 11, wherein at least one of said features has a size on the order of a wavelength of said optical radiation.

28. The system of claim 11, wherein said optical radiation is substantially normally incident on said pattern.

* * * * *